(12) United States Patent
Lindén

(10) Patent No.: US 10,955,915 B2
(45) Date of Patent: Mar. 23, 2021

(54) GAZE TRACKING VIA TRACING OF LIGHT PATHS

(71) Applicant: Tobii AB, Danderyd (SE)

(72) Inventor: Erik Lindén, Danderyd (SE)

(73) Assignee: Tobii AB, Danderyd (SE)

( * ) Notice: Subject to any disclaimer, the term of this patent is extended or adjusted under 35 U.S.C. 154(b) by 0 days.

(21) Appl. No.: 16/715,182

(22) Filed: Dec. 16, 2019

(65) Prior Publication Data

US 2020/0225744 A1 Jul. 16, 2020

(30) Foreign Application Priority Data

Dec. 17, 2018 (SE) ...................................... 1851597

(51) Int. Cl.
| | | |
|---|---|---|
| G06F 3/048 | (2013.01) | |
| G06F 3/01 | (2006.01) | |
| G06T 7/13 | (2017.01) | |
| G06T 7/70 | (2017.01) | |
| G06T 7/00 | (2017.01) | |
| H04N 5/225 | (2006.01) | |

(52) U.S. Cl.
CPC .............. G06F 3/013 (2013.01); G06F 3/017 (2013.01); G06T 7/0012 (2013.01); G06T 7/13 (2017.01); G06T 7/70 (2017.01); H04N 5/2256 (2013.01); G06T 2207/30041 (2013.01)

(58) Field of Classification Search
None
See application file for complete search history.

(56) References Cited

U.S. PATENT DOCUMENTS

| | | | | |
|---|---|---|---|---|
| 5,912,721 A | * | 6/1999 | Yamaguchi .......... | G06K 9/0061 351/209 |
| 6,204,828 B1 | * | 3/2001 | Amir ..................... | G06F 3/013 345/156 |
| 6,456,438 B1 | * | 9/2002 | Lee ....................... | G02B 27/01 359/630 |
| 7,742,623 B1 | * | 6/2010 | Moon .................. | G06K 9/00228 382/103 |
| 8,885,882 B1 | * | 11/2014 | Yin .................... | G06K 9/00248 382/103 |
| 9,898,082 B1 | * | 2/2018 | Greenwald ......... | G06K 9/00597 |
| 2003/0076300 A1 | * | 4/2003 | Lauper .................. | G06F 3/013 345/158 |

(Continued)

*Primary Examiner* — Hua Lu
(74) *Attorney, Agent, or Firm* — Samuel I. Yamron

(57) ABSTRACT

A preliminary path for light travelling towards a camera via corneal reflection is estimated based on a preliminary position and orientation of an eye. A position where the reflection would appear in images captured by the camera is estimated. A distance is formed between a detected position of a corneal reflection of an illuminator and the estimated position. A second preliminary path for light travelling through the cornea or from the sclera towards a camera is estimated based on the preliminary position and orientation, and a position where the second preliminary path would appear to originate in images captured by this camera is estimated. A distance is formed between a detected edge of a pupil or iris and the estimated position where the second preliminary path would appear to originate. An updated position and/or orientation of the eye is determined using an objective function formed based on the formed distances.

20 Claims, 14 Drawing Sheets

(56) References Cited

U.S. PATENT DOCUMENTS

| | | | |
|---|---|---|---|
| 2003/0086057 A1* | 5/2003 | Cleveland | G06K 9/0061 351/204 |
| 2003/0123027 A1* | 7/2003 | Amir | G06K 9/00604 351/209 |
| 2003/0223037 A1* | 12/2003 | Chernyak | A61F 9/00806 351/209 |
| 2004/0174496 A1* | 9/2004 | Ji | G06F 3/013 351/209 |
| 2010/0328444 A1* | 12/2010 | Blixt | A61B 3/145 348/78 |
| 2011/0069277 A1* | 3/2011 | Blixt | G06K 9/00604 351/210 |
| 2012/0113209 A1* | 5/2012 | Ritchey | G06F 3/015 348/14.02 |
| 2013/0114043 A1* | 5/2013 | Balan | A61B 3/113 351/210 |
| 2013/0169560 A1* | 7/2013 | Cederlund | G06F 3/013 345/173 |
| 2013/0188834 A1* | 7/2013 | Ebisawa | A61B 3/113 382/103 |
| 2014/0184496 A1* | 7/2014 | Gribetz | G02B 27/017 345/156 |
| 2014/0211995 A1* | 7/2014 | Model | G06F 3/013 382/103 |
| 2014/0247215 A1* | 9/2014 | George-Svahn | G06F 3/0227 345/158 |
| 2014/0247232 A1* | 9/2014 | George-Svahn | G06F 3/013 345/173 |
| 2014/0267771 A1* | 9/2014 | Lawler | G06K 9/00597 348/169 |
| 2014/0354539 A1* | 12/2014 | Skogo | G06F 3/0304 345/156 |
| 2015/0077543 A1* | 3/2015 | Kerr | H04N 5/2256 348/135 |
| 2015/0278599 A1* | 10/2015 | Zhang | G06T 7/80 348/78 |
| 2016/0042501 A1* | 2/2016 | Huang | G02B 27/0075 345/428 |
| 2016/0065903 A1* | 3/2016 | Wang | G06F 3/013 348/148 |
| 2016/0066781 A1* | 3/2016 | Thompson | A61B 3/145 600/476 |
| 2016/0202756 A1* | 7/2016 | Wu | G06F 3/013 382/103 |
| 2016/0270655 A1* | 9/2016 | Caraffi | A61B 3/0025 |
| 2016/0317012 A1* | 11/2016 | Bagherinia | G06T 7/70 |
| 2017/0115742 A1* | 4/2017 | Xing | G06F 3/0485 |
| 2017/0119298 A1* | 5/2017 | Cheung | G06K 9/00248 |
| 2017/0123489 A1* | 5/2017 | Guenter | G06T 19/006 |
| 2017/0123492 A1* | 5/2017 | Marggraff | H04N 5/247 |
| 2017/0132496 A1* | 5/2017 | Shoaib | G06K 9/66 |
| 2017/0188823 A1* | 7/2017 | Ganesan | G02B 27/0093 |
| 2017/0372487 A1* | 12/2017 | Lagun | G06T 7/11 |
| 2018/0007255 A1* | 1/2018 | Tang | G06K 9/00604 |
| 2018/0081434 A1* | 3/2018 | Siddiqui | G06F 3/013 |
| 2018/0113311 A1* | 4/2018 | Klug | H04N 13/128 |
| 2018/0279960 A1* | 10/2018 | Li | A61B 5/7207 |
| 2018/0357790 A1* | 12/2018 | Kojima | G06K 9/0061 |
| 2019/0015237 A1* | 1/2019 | Agrawal | A61H 1/0296 |
| 2019/0110037 A1* | 4/2019 | Lukac | H01L 27/14621 |
| 2019/0147607 A1* | 5/2019 | Stent | G06T 7/73 382/103 |
| 2020/0124844 A1* | 4/2020 | Ortiz Egea | G06K 9/00597 |

* cited by examiner

GAZE TRACKING VIA TRACING OF LIGHT PATHS

CROSS-REFERENCES TO RELATED APPLICATIONS

This application claims priority to Swedish Application No. 1851597-3, filed Dec. 17, 2018; the content of which are hereby incorporated by reference.

TECHNICAL FIELD

The present disclosure generally relates to gaze tracking.

BACKGROUND

Different techniques have been developed for monitoring in which direction (or at which point on a display) a user is looking. This is often referred to as gaze tracking or eye tracking. Such techniques often involve detection of certain features in images of the eye, and a gaze direction or gaze point is then computed based on positions of these detected features. An example of such a gaze tracking technique is pupil center corneal reflection (PCCR). PCCR-based gaze tracking employs the position of the pupil center and the position of glints (reflections of illuminators at the cornea) to compute a gaze direction of the eye or a gaze point at a display.

Good gaze tracking performance is often important for the user experience. The estimated gaze point (or gaze direction) should for example be accurate, and it should not lag behind the true gaze point (or gaze direction) to such an extent that this effect is noticeable to the user. Several factors may affect gaze tracking performance. Properties of the eyes may differ between different people, and even between the left and right eye of a person. Such differences may at least to some extent be handled via calibration of an eye model to the specific user. Still, the eye model is only an approximation of the real eye, so some deviation from the true gaze point (or gaze direction) may occur. The presence of glasses, contact lenses, and/or a tear film at the eye may also affect gaze tracking performance, for example through distortion of the images of the eye employed for the gaze tracking.

It would be desirable to provide new ways to address one or more of the abovementioned issues.

SUMMARY

Methods, systems and computer-readable storage media having the features defined in the independent claims are provided for addressing one or more of the abovementioned issues. Preferable embodiments are defined in the dependent claims.

Hence, a first aspect provides embodiments of a gaze tracking method. The method comprises obtaining one or more images of an eye. An image of the one or more images has been captured by a camera at a time instance (or at a point in time) while the eye was illuminated by an illuminator. The image captured by the camera shows a first reflection of the illuminator at a cornea of the eye. An image of the one or more images has been captured by a camera at the time instance (or at the point in time) and shows at least a portion of an edge. The edge is an edge of a pupil of the eye, or an edge of an iris of the eye. The method comprises detecting a position of the first reflection in the image showing the first reflection, detecting at least a portion of the edge in the image showing at least a portion of the edge, and obtaining a preliminary position of the eye in space and a preliminary orientation of the eye in space. The method comprises estimating, based on the preliminary position of the eye and the preliminary orientation of the eye, a first preliminary path for light travelling, via a reflection at the cornea, towards the camera by which the image showing the first reflection was captured. The method comprises estimating (or predicting) a position where the reflection from the first preliminary path would appear in images of the eye captured by the camera by which the image showing the first reflection was captured. The method comprises forming a first distance between the detected position of the first reflection in the image showing the first reflection and the estimated position where the reflection from the first preliminary path would appear. The method comprises estimating, based on the preliminary position of the eye and the preliminary orientation of the eye, a second preliminary path for light travelling through at least a portion of the cornea of the eye towards the camera by which the image showing at least a portion of the edge was captured or for light travelling from a sclera of the eye towards the camera by which the image showing at least a portion of the edge was captured. The method comprises estimating a position where the second preliminary path would appear to originate in images of the eye captured by the camera by which the image showing at least a portion of the edge was captured. The method comprises forming a second distance between the edge and the estimated position where the second preliminary path would appear to originate. The method comprises forming an objective function based on at least the first and second distances, and determining, using the objective function, an updated (or new) position of the eye in space and/or an updated (or new) orientation of the eye in space.

The proposed gaze tracking method (which involves estimating the first and second preliminary paths based on the preliminary position and orientation of the eye, and determining an updated position of the eye and/or an updated orientation of the eye using the objective function) facilitates taking into account how light travelling towards the camera may be affected by various factors on its way towards the camera. Examples of such factors which could be taken into account are refraction at glasses, and/or how light is reflected at the cornea (for example using a non-spherical cornea model), and/or refraction at the cornea. Such factors may be difficult to handle in traditional gaze tracking methods. Some traditional gaze tracking methods simply ignore such factors (hoping that gaze tracking performance will still be acceptable), while other gaze tracking methods attempt to deal with such factors via various approximation schemes. The proposed gaze tracking method provides a convenient framework for dealing with such factors.

It will be appreciated that the image showing the first reflection need not necessarily coincide with the image showing at least a portion of the edge. The image showing the first reflection may for example have been captured by a first camera, and the image showing at least a portion of the edge may for example have been captured by a second camera which is distinct from the first camera.

It will also be appreciated that the objective function may for example be a cost function or a loss function.

A second aspect provides embodiments of a gaze tracking system comprising processing circuitry (or one or more processors) configured to:

obtain one or more images of an eye, wherein an image of the one or more images has been captured by a camera at a time instance while the eye was illuminated by an illuminator, wherein the image captured by the camera shows a first reflection of the illuminator at a cornea of the eye, wherein an image of the one or more images has been captured by a camera at the time instance and shows at least a portion of an edge, wherein the edge is:
an edge of a pupil of the eye; or
an edge of an iris of the eye;
detect a position of the first reflection in the image showing the first reflection;
detect at least a portion of the edge in the image showing at least a portion of the edge;
obtain a preliminary position of the eye in space and a preliminary orientation of the eye in space;
estimate, based on the preliminary position of the eye and the preliminary orientation of the eye, a first preliminary path for light travelling, via a reflection at the cornea, towards the camera by which the image showing the first reflection was captured;
estimate a position where the reflection from the first preliminary path would appear in images of the eye captured by the camera by which the image showing the first reflection was captured;
form a first distance between the detected position of the first reflection in the image showing the first reflection and the estimated position where the reflection from the first preliminary path would appear;
estimate, based on the preliminary position of the eye and the preliminary orientation of the eye, a second preliminary path for light travelling through at least a portion of the cornea of the eye towards the camera by which the image showing at least a portion of the edge was captured or for light travelling from a sclera of the eye towards the camera by which the image showing at least a portion of the edge was captured;
estimate a position where the second preliminary path would appear to originate in images of the eye captured by the camera by which the image showing at least a portion of the edge was captured;
form a second distance between the edge and the estimated position where the second preliminary path would appear to originate;
form an objective function based on at least the first and second distances; and
determine, using the objective function, an updated position of the eye in space and/or an updated orientation of the eye in space.

The processing circuitry (or one or more processors) may for example be configured to perform the method as defined in any of the embodiments of the first aspect disclosed herein (in other words, in the claims, the summary, or the detailed description). The system may for example comprise one or more non-transitory computer-readable storage media (or one or more memories) storing instructions that, upon execution by the processing circuitry (or one or more processors), cause the gaze tracking system to perform the method as defined in any of the embodiments of the first aspect disclosed herein.

The effects and/or advantages presented in the present disclosure for embodiments of the method according to the first aspect may also apply to corresponding embodiments of the system according to the second aspect.

A third aspect provides embodiments of a non-transitory computer-readable storage medium storing instructions which, when executed by a gaze tracking system, cause the gaze tracking system to:

obtain one or more images of an eye, wherein an image of the one or more images has been captured by a camera at a time instance while the eye was illuminated by an illuminator, wherein the image captured by the camera shows a first reflection of the illuminator at a cornea of the eye, wherein an image of the one or more images has been captured by a camera at the time instance and shows at least a portion of an edge, wherein the edge is:
an edge of a pupil of the eye; or
an edge of an iris of the eye;
detect a position of the first reflection in the image showing the first reflection;
detect at least a portion of the edge in the image showing at least a portion of the edge;
obtain a preliminary position of the eye in space and a preliminary orientation of the eye in space;
estimate, based on the preliminary position of the eye and the preliminary orientation of the eye, a first preliminary path for light travelling, via a reflection at the cornea, towards the camera by which the image showing the first reflection was captured;
estimate a position where the reflection from the first preliminary path would appear in images of the eye captured by the camera by which the image showing the first reflection was captured;
form a first distance between the detected position of the first reflection in the image showing the first reflection and the estimated position where the reflection from the first preliminary path would appear;
estimate, based on the preliminary position of the eye and the preliminary orientation of the eye, a second preliminary path for light travelling through at least a portion of the cornea of the eye towards the camera by which the image showing at least a portion of the edge was captured or for light travelling from a sclera of the eye towards the camera by which the image showing at least a portion of the edge was captured;
estimate a position where the second preliminary path would appear to originate in images of the eye captured by the camera by which the image showing at least a portion of the edge was captured;
form a second distance between the edge and the estimated position where the second preliminary path would appear to originate;
form an objective function based on at least the first and second distances; and
determine, using the objective function, an updated position of the eye in space and/or an updated orientation of the eye in space.

The non-transitory computer-readable storage medium may for example store instructions which, when executed by a gaze tracking system (or by processing circuitry comprised in the gaze tracking system), cause the gaze tracking system to perform the method as defined in any of the embodiments of the first aspect disclosed herein (in other words, in the claims, the summary, or the detailed description).

The non-transitory computer-readable storage medium may for example be provided in a computer program product. In other words, a computer program product may for example comprise a non-transitory computer-readable storage medium storing instructions which, when executed by a gaze tracking system, cause the gaze tracking system to perform the method as defined in any of the embodiments of the first aspect disclosed herein.

The effects and/or advantages presented in the present disclosure for embodiments of the method according to the first aspect may also apply to corresponding embodiments of the non-transitory computer-readable storage medium according to the third aspect.

It is noted that embodiments of the present disclosure relate to all possible combinations of features recited in the claims.

BRIEF DESCRIPTION OF THE DRAWINGS

In what follows, example embodiments will be described in greater detail with reference to the accompanying drawings, on which.

All the figures are schematic, not necessarily to scale, and generally only show parts which are necessary in order to elucidate the respective embodiments, whereas other parts may be omitted or merely suggested. Any reference number appearing in multiple drawings refers to the same object or feature throughout the drawings, unless otherwise indicated.

DETAILED DESCRIPTION

It will be appreciated that throughout the present disclosure, the term camera relates to any type of imaging device, image sensor, or the like, which is configured to generate an image based on received light.

Gaze tracking methods as well as corresponding systems and storage media will be described below with reference to FIGS. 3-20. First, certain features of an eye will be described with reference to FIGS. 1-2.

The Eye

Figure 1:
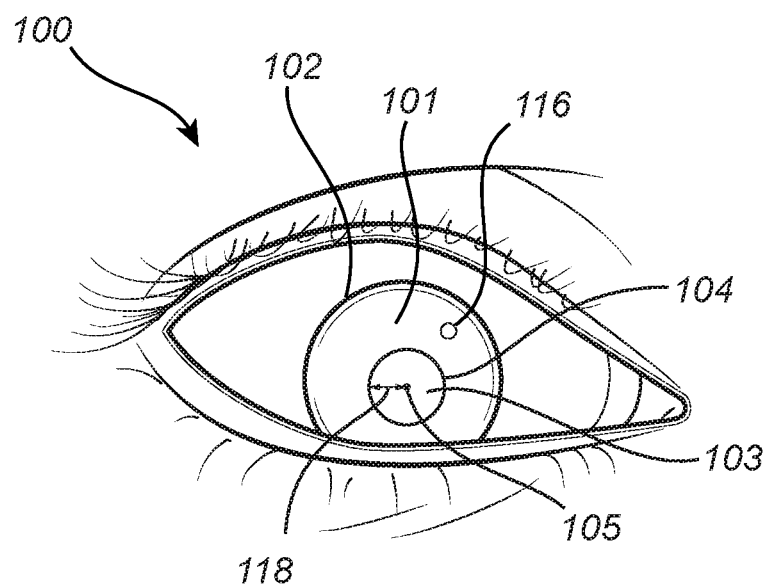
FIG. 1 is a front view of an eye.
Figure 2:
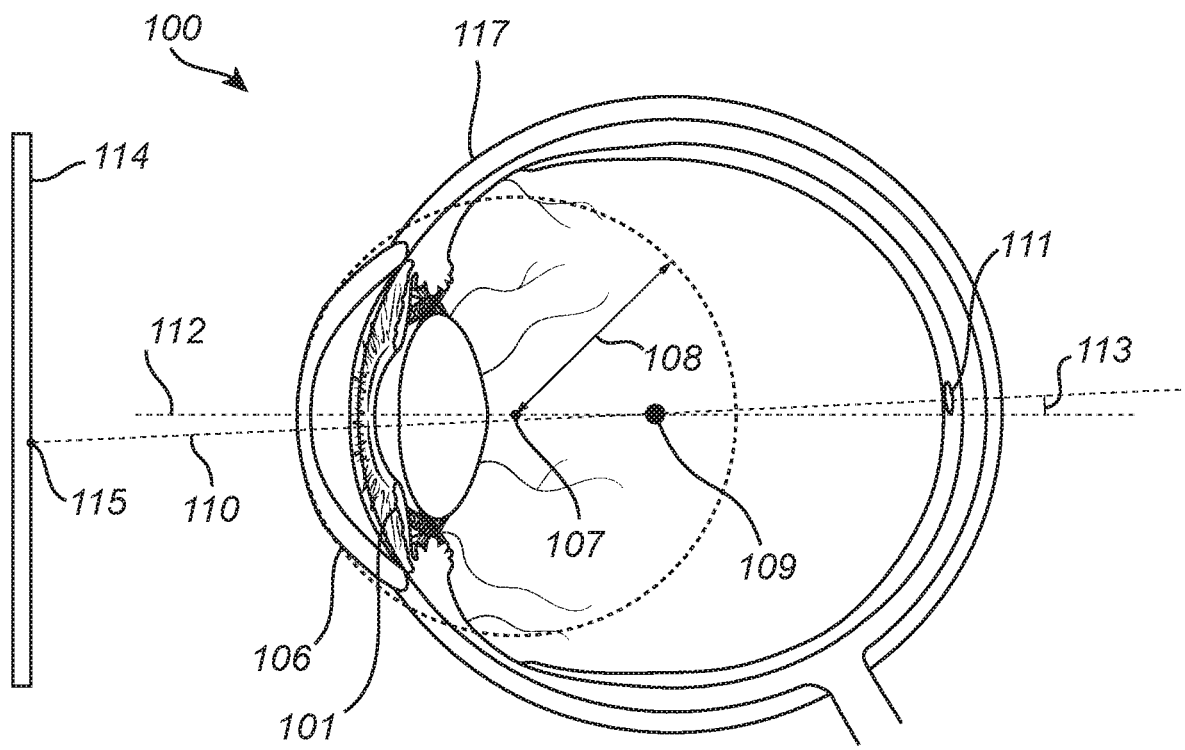
FIG. 2 is a cross sectional view of the eye from FIG. 1 from the side of the eye.

FIG. 1 is a front view of an eye 100. FIG. 2 is a cross sectional view of the eye 100 from the side of the eye 100. While FIG. 2 shows more or less the entire eye 100, the front view presented in FIG. 1 only shows those parts of the eye 100 which are typically visible from in front of a person's face. The eye 100 has an iris 101 which has an outer edge 102. The eye 100 has a pupil 103, which has a pupil edge 104, a pupil center 105, and a pupil radius 118. The eye 100 also has a cornea 106 which is curved and has a center of curvature 107 which is referred to as the center 107 of corneal curvature, or simply the cornea center 107. The cornea 106 has a radius of curvature referred to as the radius 108 of the cornea 106, or simply the cornea radius 108. The eye 100 has a center 109 which may also be referred to as the center 109 of the eye ball, or simply the eye ball center 109. The visual axis 110 of the eye 100 passes through the center 109 of the eye 100 to the fovea 111 of the eye 100. The optical axis 112 of the eye 100 passes through the pupil center 105 and the center 109 of the eye 100. The visual axis 110 forms an angle 113 relative to the optical axis 112. The deviation or offset between the visual axis 110 and the optical axis 112 is often referred to as the fovea offset 113. In the example shown in FIG. 2, the eye 100 is looking towards a display 114, and the eye 100 is gazing at a gaze point 115 at the display 114. FIG. 1 also shows a reflection 116 of an illuminator at the cornea 106. Such a reflection 116 is also known as a glint 116. The eye 100 also has a sclera 117.

Gaze Tracking System

Figure 3:
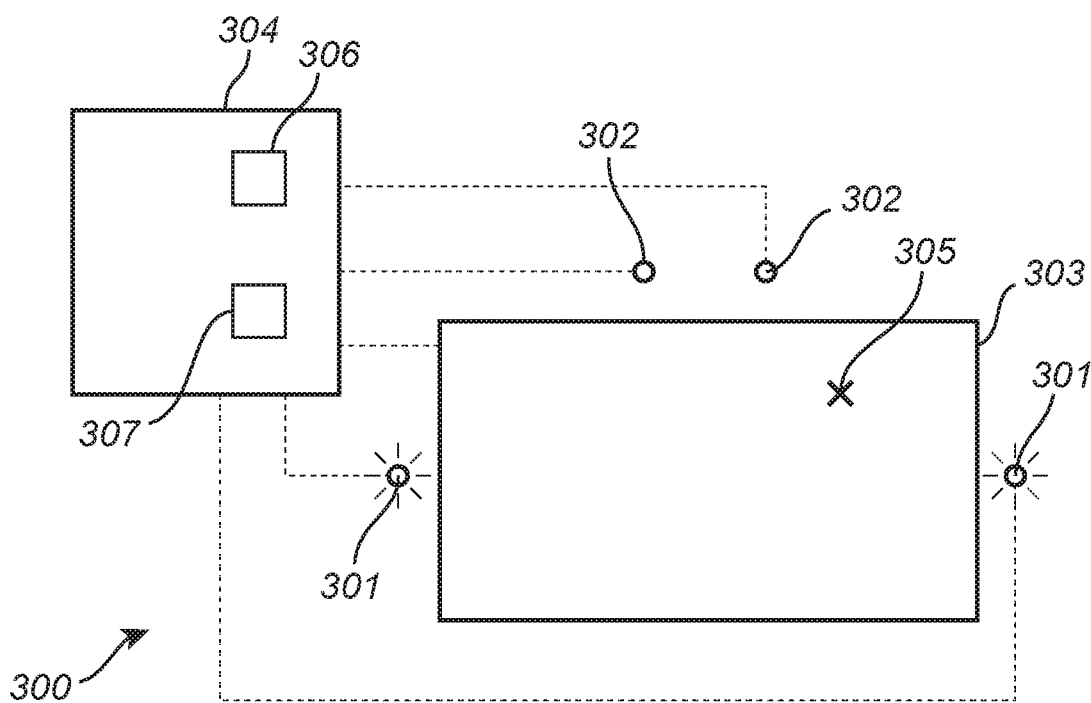
FIG. 3 is a schematic overview of a gaze tracking system, according to an embodiment.

FIG. 3 is a schematic overview of a gaze tracking system 300, according to an embodiment. The system 300 comprises one or more illuminators 301 (or light sources) for illuminating the eye 100 and one or more cameras 302 (or image sensors) for capturing images of the eye 100 while the eye 100 looks at a display 303 (which may for example be the display 114 shown in FIG. 2). The illuminator(s) 301 are arranged at known position(s) relative to the camera(s) 302. The illuminator(s) 301 and the camera(s) 302 may for example be are arranged at known position(s) relative to the display 303. The system 300 also comprises processing circuitry 304 configured to perform a gaze tracking method, according to an embodiment. The processing circuitry 304 may for example estimate a gaze direction (or gaze vector) of the eye 100 (corresponding to a direction of the visual axis 110), or a gaze point of the eye 100 at the display 303 (like the gaze point 115 at the display 114 shown in FIG. 2).

The processing circuitry 304 is communicatively connected to the illuminators 301 and the cameras 302, for example via a wired or wireless connection. The processing circuitry 304 may also be communicatively connected to the display 303, for example for controlling (or triggering) the display 303 to show test stimulus points 305 for calibration of the gaze tracking system 300.

The illuminators 301 may for example be infrared or near infrared illuminators, for example in the form of light emitting diodes (LEDs). However, other types of illuminators may also be envisaged. FIG. 3 shows example illuminators 301 located at either side of the display 303, but the illuminators 301 could be located elsewhere. The system 300 may for example comprise illuminators 301 distributed around the display 303.

The cameras 302 may for example be charged-coupled device (CCD) cameras or Complementary Metal Oxide Semiconductor (CMOS) cameras. However, other types of cameras may also be envisaged. FIG. 3 shows example cameras 302 located above the display 303, but the cameras 302 could be located elsewhere, for example below the display 303. The system 300 may for example comprise cameras 302 distributed around the display 303.

The display 303 may for example be a liquid-crystal display (LCD) or a LED display. However, other types of displays may also be envisaged. The display 303 may for example be flat or curved. The display 303 may for example be a TV screen, a computer screen, or may be part of a head-mounted device such as a virtual reality (VR) or augmented reality (AR) device. The display 303 may for example be placed in front of one of the user's eyes. In other words, separate displays 303 may be employed for the left and right eyes. Separate gaze tracking equipment (such as illuminators 301 and cameras 302) may for example be employed for the left and right eyes.

The processing circuitry 304 may be employed for gaze tracking for both eyes, or there may be separate processing circuitry 304 for the left and right eyes. The gaze tracking system 300 may for example perform gaze tracking for the left and right eyes separately, and may then determine a combined gaze point as an average of the gaze points for the left and right eyes.

The processing circuitry 304 may for example comprise one or more processors 306. The processor(s) 306 may for example be application-specific integrated circuits (ASIC) configured to perform a specific gaze tracking method. Alternatively, the processor(s) 306 may configured to execute instructions (for example in the form of a computer program) stored in one or more memories 307. Such a memory 307 may for example be comprised in the circuitry 304 of the gaze tracking system 300, or may be external to (for example located remotely from) the gaze tracking system 300. The memory 307 may store instructions for causing the gaze tracking system 300 to perform a gaze tracking method.

It will be appreciated that the gaze tracking system 300 described above with reference to FIG. 3 is provided as an example, and that many other gaze tracking systems may be envisaged. For example, the illuminators 301 and/or the cameras 302 need not necessarily be regarded as part of the gaze tracking system 300. The gaze tracking system 300 may for example consist only of the processing circuitry 304. The display 303 may for example be comprised in the gaze tracking system 300, or may be regarded as separate from the gaze tracking system 300.

Light Paths and Predicted Features in Images

Figure 4:
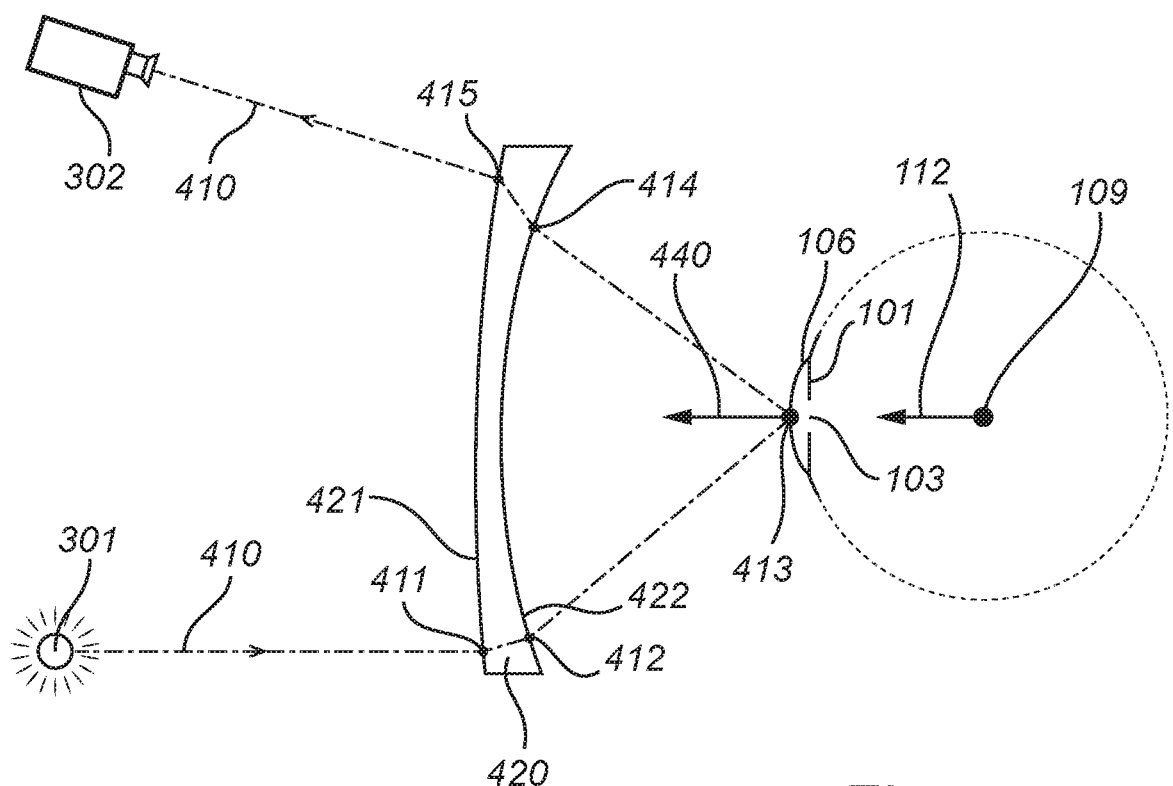
FIG. 4 is a schematic overview of a path for light travelling from an illuminator to a camera via a reflection at a cornea an eye.

FIG. 4 is a schematic overview of a path 410 for light travelling from the illuminator 301 to the camera 302 via a reflection at the cornea 106 of the eye 100.

In the example shown in FIG. 4, the user wears glasses 420. The example path 410 shown in FIG. 4 leaves the illuminator 301 and reaches a first surface 421 of the glasses 420 at a point 411. The light is refracted at the point 411. The light then reaches a second surface 422 of the glasses 420 at a point 412 and is refracted there again. The light then reaches the cornea 106 at a point 413 where it is reflected. A normal vector 440 may be employed to compute the reflection. An example approach for computing the reflection will be described further below with referent to FIG. 18. After reflection at the cornea 106, the light reaches the second surface 422 of the glasses 420 at a point 414 where it is refracted. The light passes through the glasses 420 and reaches the first surface 421 of the glasses 420 at a point 415 where it is refracted again. The light then reaches the camera 302. The refractions at the points 411, 412, 414 and 415 may be computed via Snell's law. Depending where the eye 100 is located in space (which may be defined via the position 109 of the center of the eye 100), and how the eye 100 is oriented in space (which may be defined via the optical axis 112), the point of reflection 413 (or glint) may appear at different positions in images of the eye 100 captured by the camera 302. Hence, glint positions may be predicted for different positions and orientations of the eye 100, and may then be compared with an observed glint position in an image captured by the camera 302, as part of a method for determining the true position and orientation of the eye 100 in space.

Figure 5:
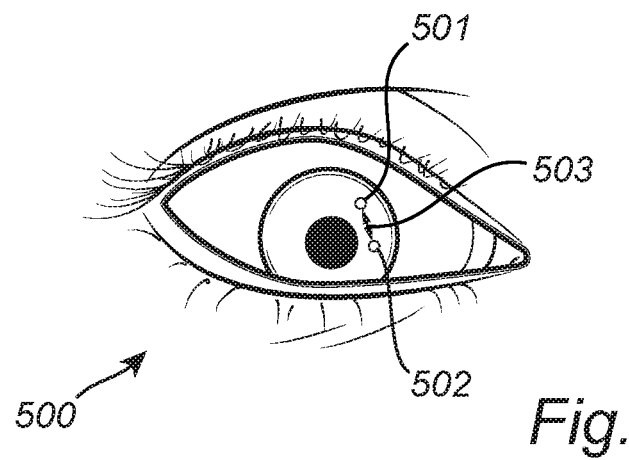
FIG. 5 is an example image of an eye showing a detected glint position and a glint position predicted using the path from FIG. 4.

FIG. 5 is an example image 500 of the eye 100 showing a glint position 501 detected in the image and a glint position 502 predicted via the path 410 in FIG. 4. The predicted glint position 502 is located a distance 503 away from the detected glint position 501. If the position and orientation of the eye 100 employed for computing the path 410 is correct, this distance 503 should be relatively small. Although the distance 503 may in theory be zero, noise may affect the accuracy of the detected position 501, and approximations and/or simplifications may be employed when computing how the light would be refracted and reflected along the path 410, which may affect the accuracy of the predicted glint position 502.

Figure 6:
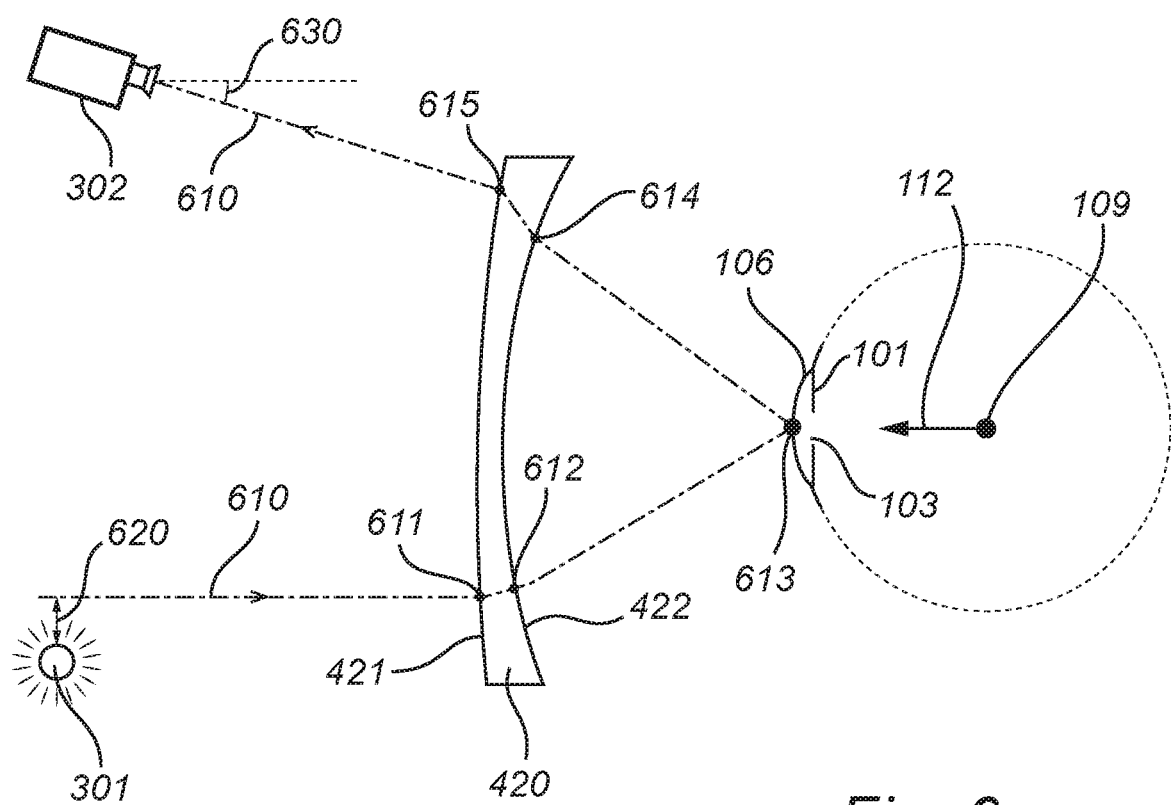
FIG. 6 is a schematic overview of a path for light travelling to a camera via a reflection at a cornea of an eye.

FIG. 6 is a schematic overview of a path 610 for light travelling to the camera 302 via a reflection at the cornea 106 of the eye 100. In contrast to the path 410 shown in FIG. 4, the path 610 in FIG. 6 does not originate at the illuminator 301. The path 610 passes by the illuminator 301 at a distance 620. Similarly to the light path 410 in FIG. 4, the light path 610 is refracted at points 611, 612, 614 and 615 and is reflected at a point 613 at the cornea 106. The light path 610 reaches the camera 302 at a certain direction, which is illustrated herein by an angle 630. Although only the angle 630 is shown in FIG. 6, it will be appreciated that a direction in 3D space may be defined via two different angles (for example by the two angles in a spherical coordinate system). By appropriately selecting the direction at which the path 610 is to reach the camera 302, one may decrease the distance 620, or even find a path that originates at the illuminator 301, like the path 410 in FIG. 4. Although the path 610 does not actually come from the illuminator 301, a projection into the camera 302 may still be computed, so as to obtain a predicted glint position for the path 620, in analogy with the predicted glint position 502 of the path 410 shown in FIG. 5.

Figure 7:
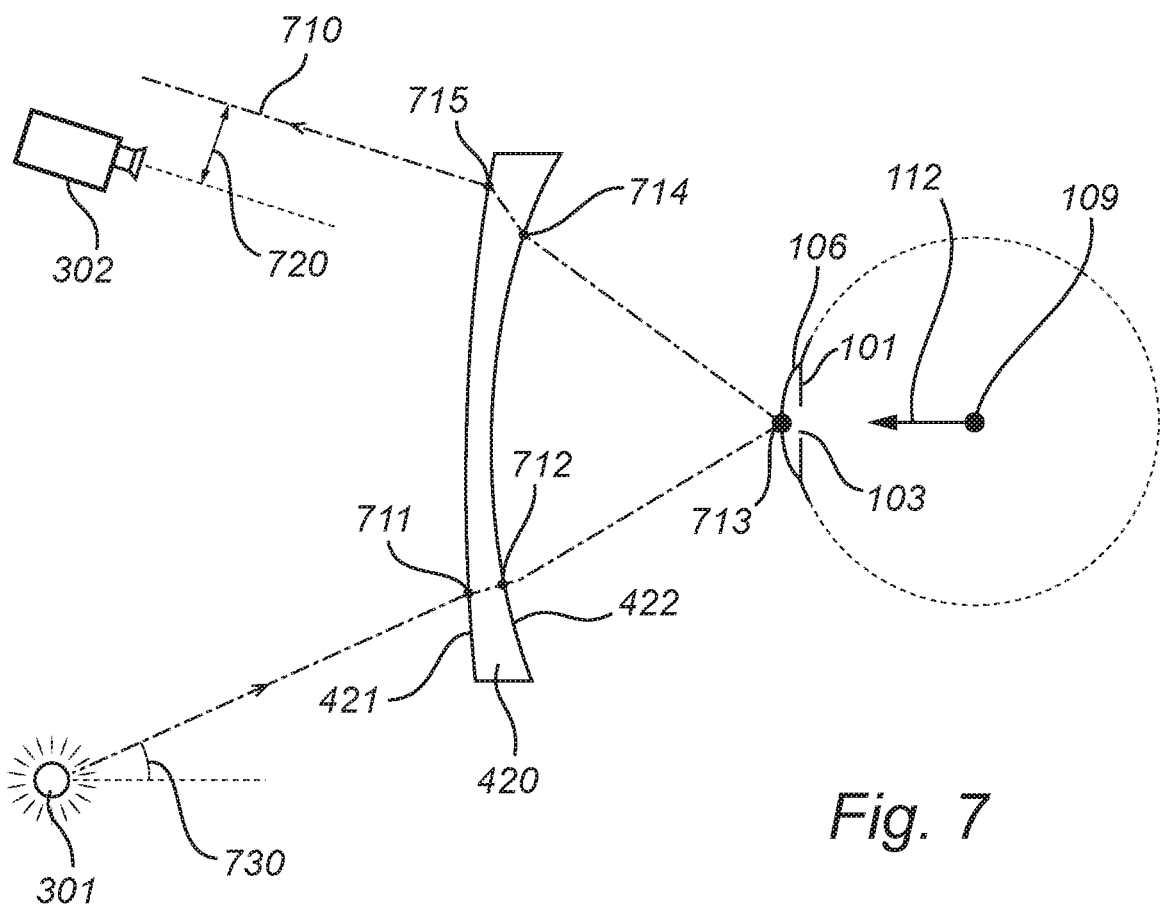
FIG. 7 is a schematic overview of a path for light travelling from an illuminator, via a reflection at a cornea of an eye, towards a camera.

FIG. 7 is a schematic overview of a path 710 for light travelling from the illuminator 301 towards the camera 302 via a reflection at the cornea 106 of the eye 100. In contrast to the path 410 shown in FIG. 4, the path 710 in FIG. 7 does not actually reach into the camera 302. The path 710 passes by the camera 302 at a distance 720. Similarly to the light path 410 in FIG. 4, the light path 710 is refracted at points 711, 712, 714 and 715 and is reflected at a point 713 at the cornea 106. The light path 710 leaves the illuminator 301 at a certain direction, which is illustrated herein by an angle 730. Although only the angle 730 is shown in FIG. 7, it will be appreciated that a direction in 3D space may be defined via two different angles (for example by the two angles in a spherical coordinate system). By appropriately selecting the direction at which the path 710 leaves the illuminator 301, one may decrease the distance 720 or even find a path that reaches the camera 302, like the path 410 in FIG. 4. Although the path 710 does not actually reach into the camera 302, a projection into the camera 302 may still be computed, so as to obtain a predicted glint position for the path 720, in analogy with the predicted glint position 502 of the path 410 shown in FIG. 5.

Figure 8:
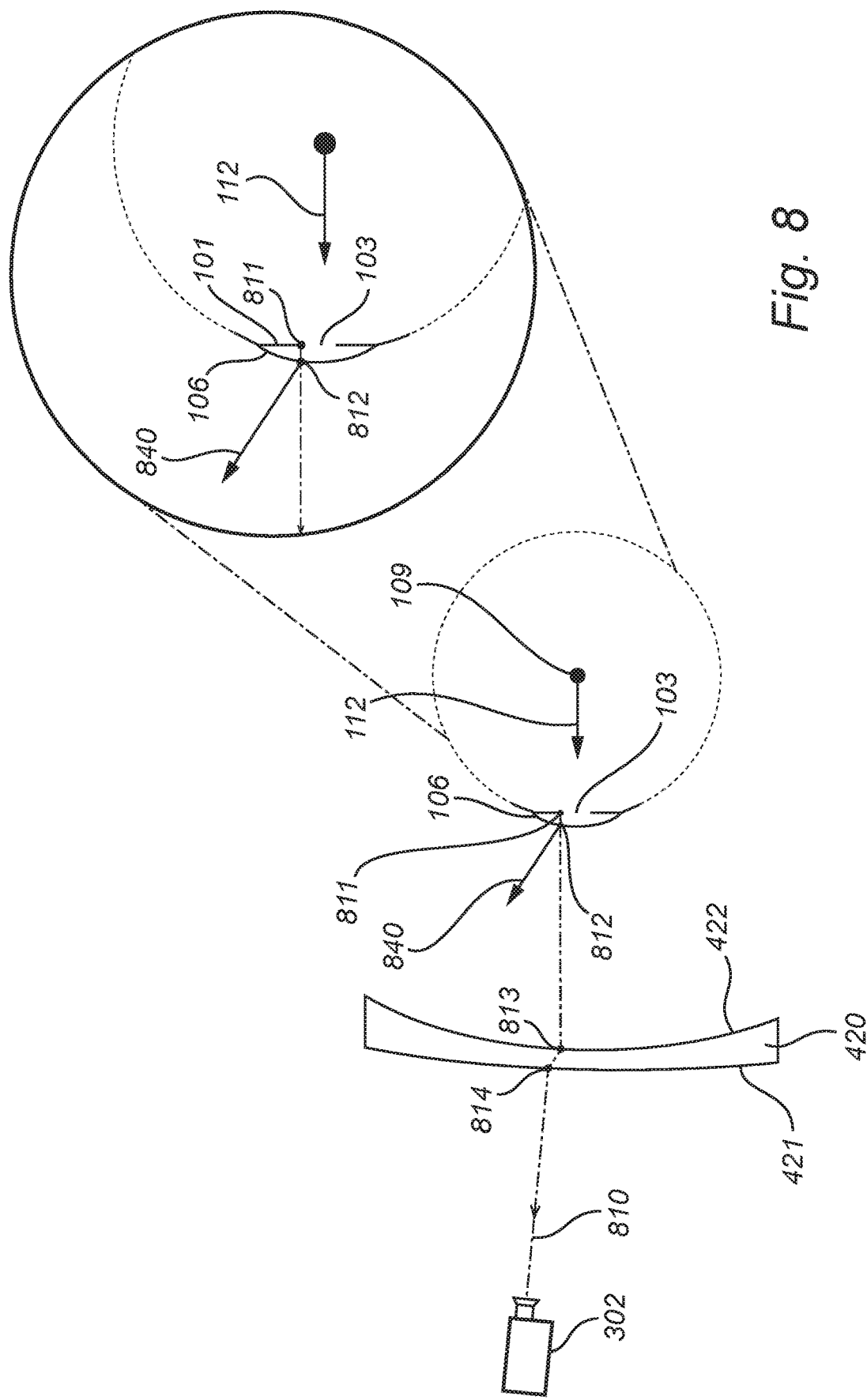
FIG. 8 is a schematic overview of a path for light travelling from an edge of a pupil of an eye, through a cornea of the eye, to a camera.

FIG. 8 is a schematic overview of a path 810 for light travelling from a point 811 along the edge 104 (the edge 104 is shown in FIG. 1) of the pupil 103 of the eye 100 to the camera 302. In the example shown in FIG. 8, the user wears glasses 420. The example path 810 shown in FIG. 8 leaves the point 811 at the edge 104 of the pupil 103 and passes through the cornea 106. The light is refracted at a point 812 where it leaves the cornea 106. A normal vector 840 may be employed to compute the refraction. An example approach for computing the refraction will be described further below with referent to FIG. 20. The light then reaches the second surface 422 of the glasses 420 at a point 813. The light is refracted at the point 813. The light then reaches the first surface 421 of the glasses 420 at a point 814 and is refracted there again. The light then reaches the camera 302. Depending where the eye 100 is located in space (which may be defined via the position 109 of the center of the eye 100), and how the eye 100 is oriented in space (which may be defined via the optical axis 112), the point 811 along the pupil edge 104 (which may be regarded as the origin of the light path 810) may appear at different positions in images of the eye 100 captured by the camera 302. Hence, pupil edge positions may be predicted for different positions and orientations of the eye 100, and may be compared with an observed pupil edge in an image captured by the camera 302, as part of a method for determining the position and orientation of the eye 100.

Figure 9:
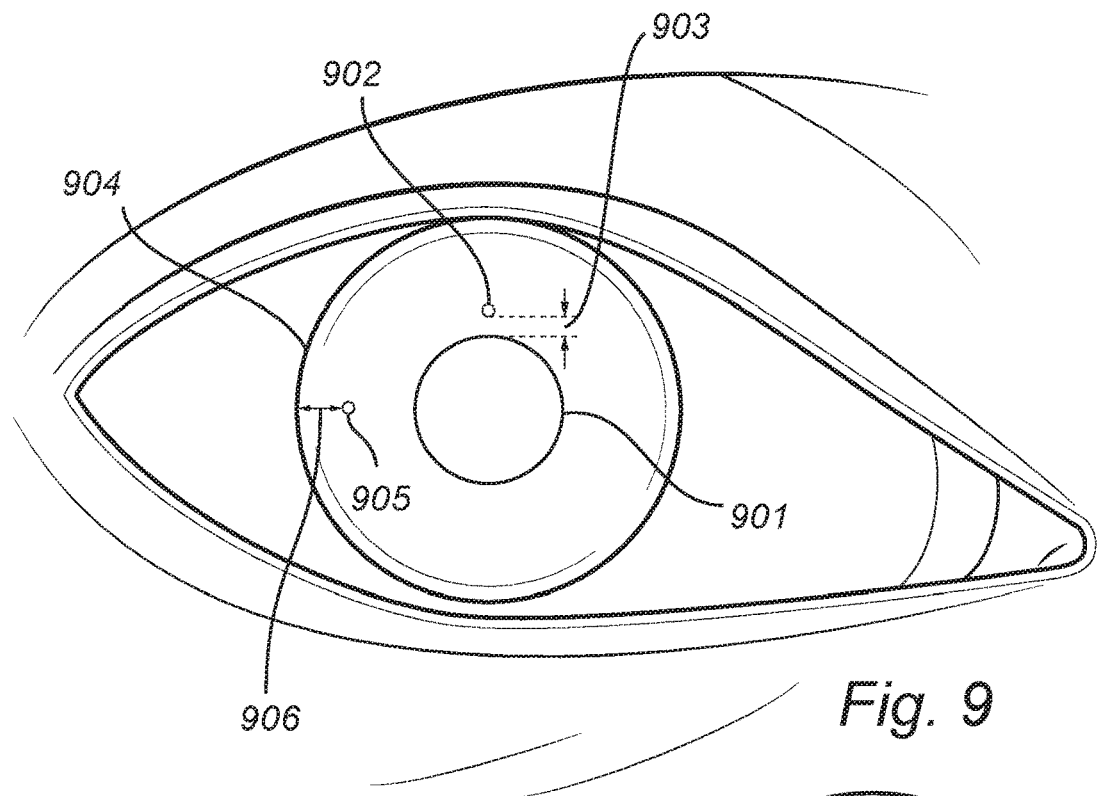
FIG. 9 is an example image of an eye showing a detected pupil edge, a position along the pupil edge predicted using the path from FIG. 8, a detected iris edge, and a position along the iris edge predicted using the path from FIG. 12.

FIG. 9 is an example image 900 of the eye 100 showing a pupil edge 901 detected in the image, and a pupil edge position 902 predicted via the light path 810 in FIG. 8. The predicted pupil edge position 902 is located a distance 903 away from the detected pupil edge 902. If the position and orientation of the eye 100 employed to compute the path 810 is correct, this distance 903 should be relatively small. Although the distance 903 may in theory be zero, noise may affect the accuracy of the detected pupil edge 901, and approximations and/or simplifications may be employed when computing how the light would be refracted along the path 810, which may affect the accuracy of the predicted position 902.

Figure 10:
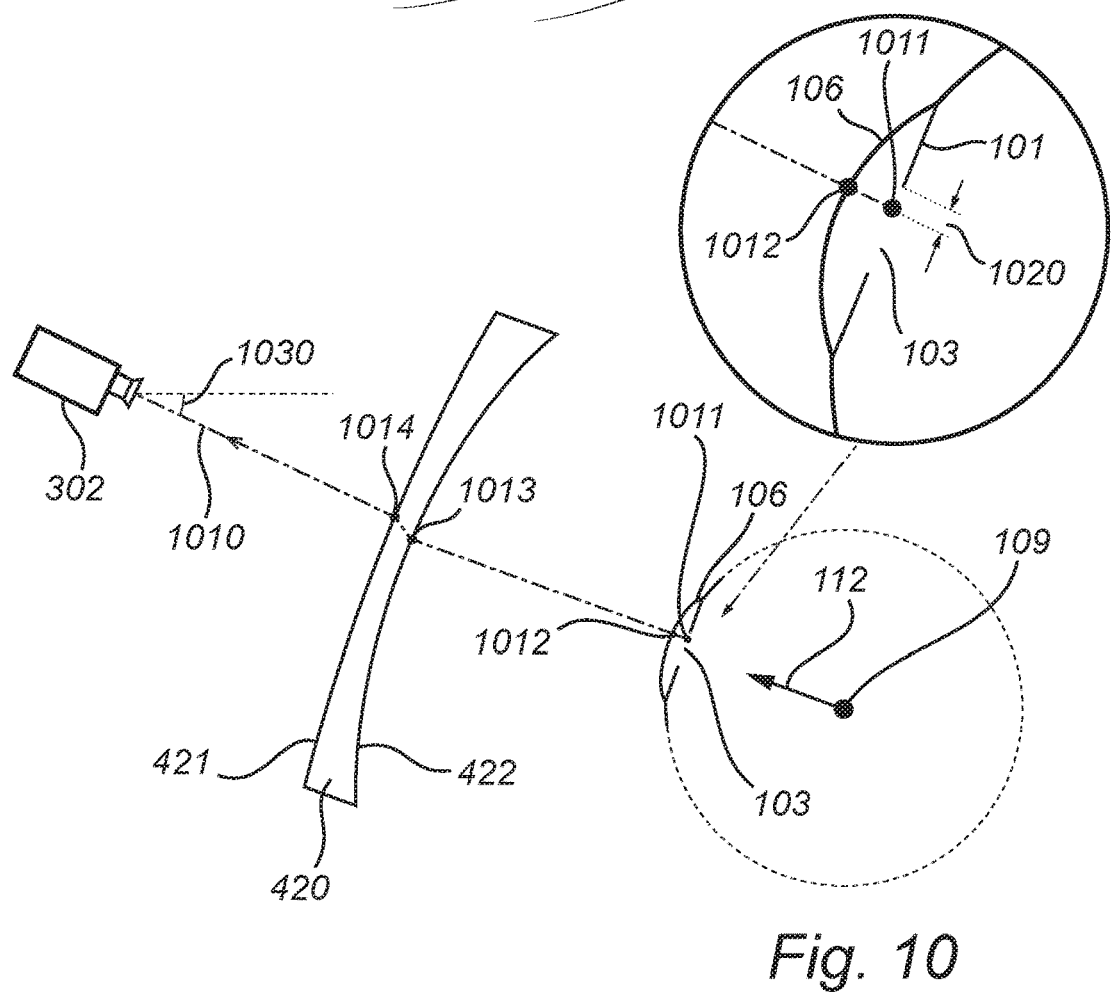
FIG. 10 is a schematic overview of a path for light travelling through a cornea of an eye to a camera.

FIG. 10 is a schematic overview of a path 1010 for light travelling through the cornea 106 of the eye 100 to the camera 302. In contrast to the path 810 shown in FIG. 8, the path 1010 in FIG. 10 does not originate at the pupil edge 104 (the pupil edge 104 is shown in FIG. 1). The path 1010 passes by the pupil edge 104 at a position 1011 located a distance 1020 from the pupil edge 104. Similarly to the light path 810 in FIG. 8, the light path 810 is refracted at points 1012, 1013, and 1014. The light path 1010 reaches the camera 302 at a certain direction, which is illustrated herein by the angle 1030. Although only the angle 1030 is shown in FIG. 10, it will be appreciated that a direction in 3D space may be defined via two different angles (for example by the two angles in a spherical coordinate system). By appropri- ately selecting the direction at which the path 1010 is to reach the camera 302, one may decrease the distance 1020, or even find a path that originates at the pupil edge 104, like the path 810 in FIG. 8. Although the path 1010 does not actually come from pupil edge 104, a projection into the camera 302 may still be computed, so as to obtain a predicted position for the path 1010, in analogy with the predicted pupil edge position 902 of the path 810 shown in FIG. 9.

Figure 11:
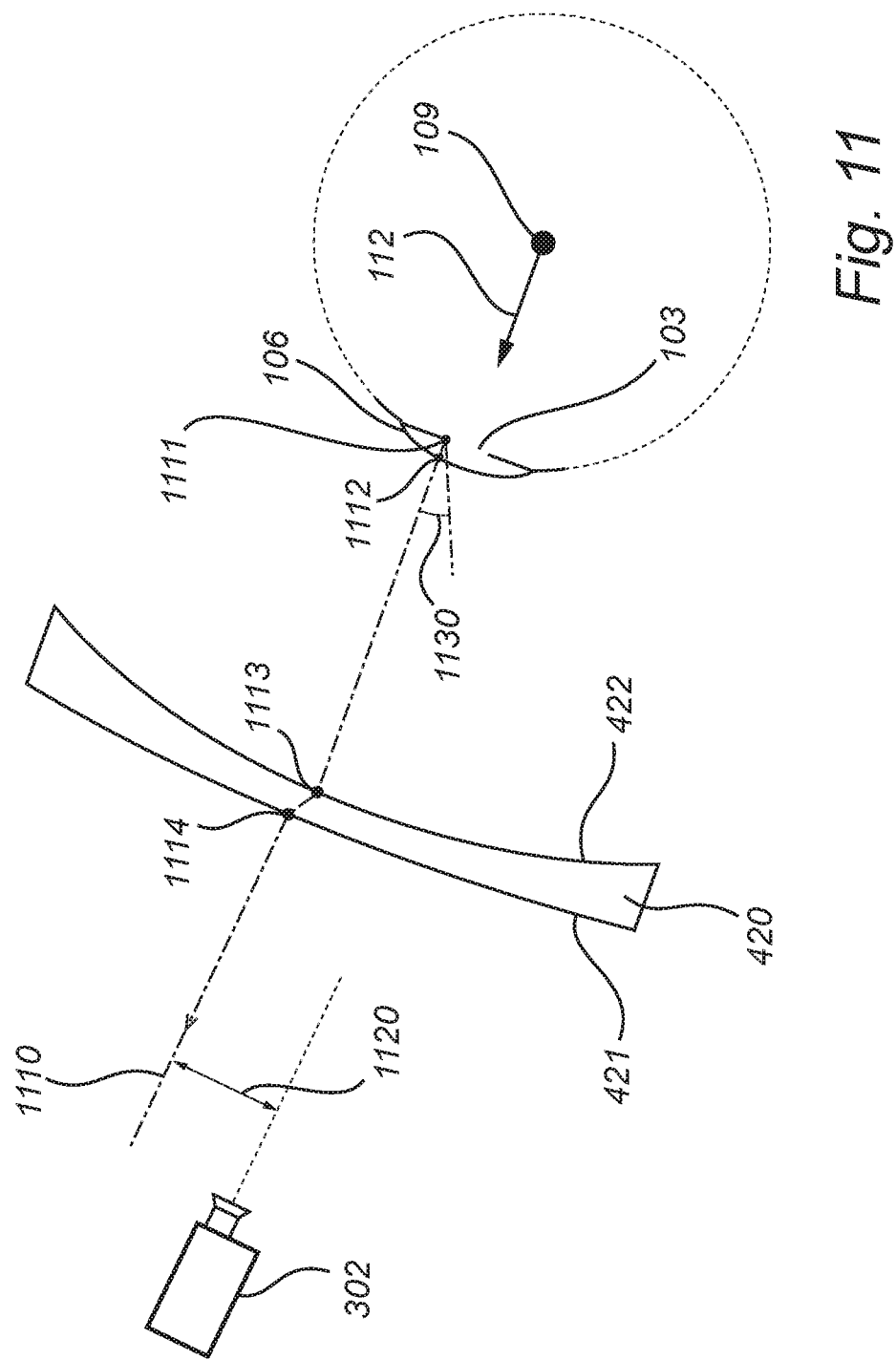
FIG. 11 is a schematic overview of a path for light travelling from the edge of a pupil of an eye, through a cornea of the eye, towards a camera.

FIG. 11 is a schematic overview of a path 1110 for light travelling from the point 1111 at the pupil edge 104 (the pupil edge 104 is shown in FIG. 1) through the cornea 106 towards the camera 302. In contrast to the path 810 shown in FIG. 8, the path 1110 in FIG. 11 does not actually reach into the camera 302. The path 1110 passes by the camera 302 at a distance 1120. The light path 1110 leaves the point 1111 at the pupil edge 104 at a certain direction, which is illustrated herein by the angle 1130. Although only the angle 1130 is shown in FIG. 11, it will be appreciated that a direction in 3D space may be defined via two different angles (for example by the two angles in a spherical coordinate system). It will be appreciated that the light path 1110 in FIG. 11 may be refracted at the point 1112 where it leaves the cornea 106, and that the angle 1130 may therefore be defined for the part of the light path 1110 located between the points 1111 and 1112. The light path 1110 will typically also be refracted at the points 1113 and 1114 where it enters and exits the glasses 420. By appropriately selecting the direction at which the path 1110 leaves the pupil edge 104, one may decrease the distance 1120, or even find a path that reaches the camera 302, like the path 810 in FIG. 8. Although the path 1110 does not actually reach into the camera 302, a projection into the camera 302 may still be computed, so as to obtain a predicted position for the path 1010, in analogy with the predicted pupil edge position 902 of the path 810 shown in FIG. 9.

Figure 12:
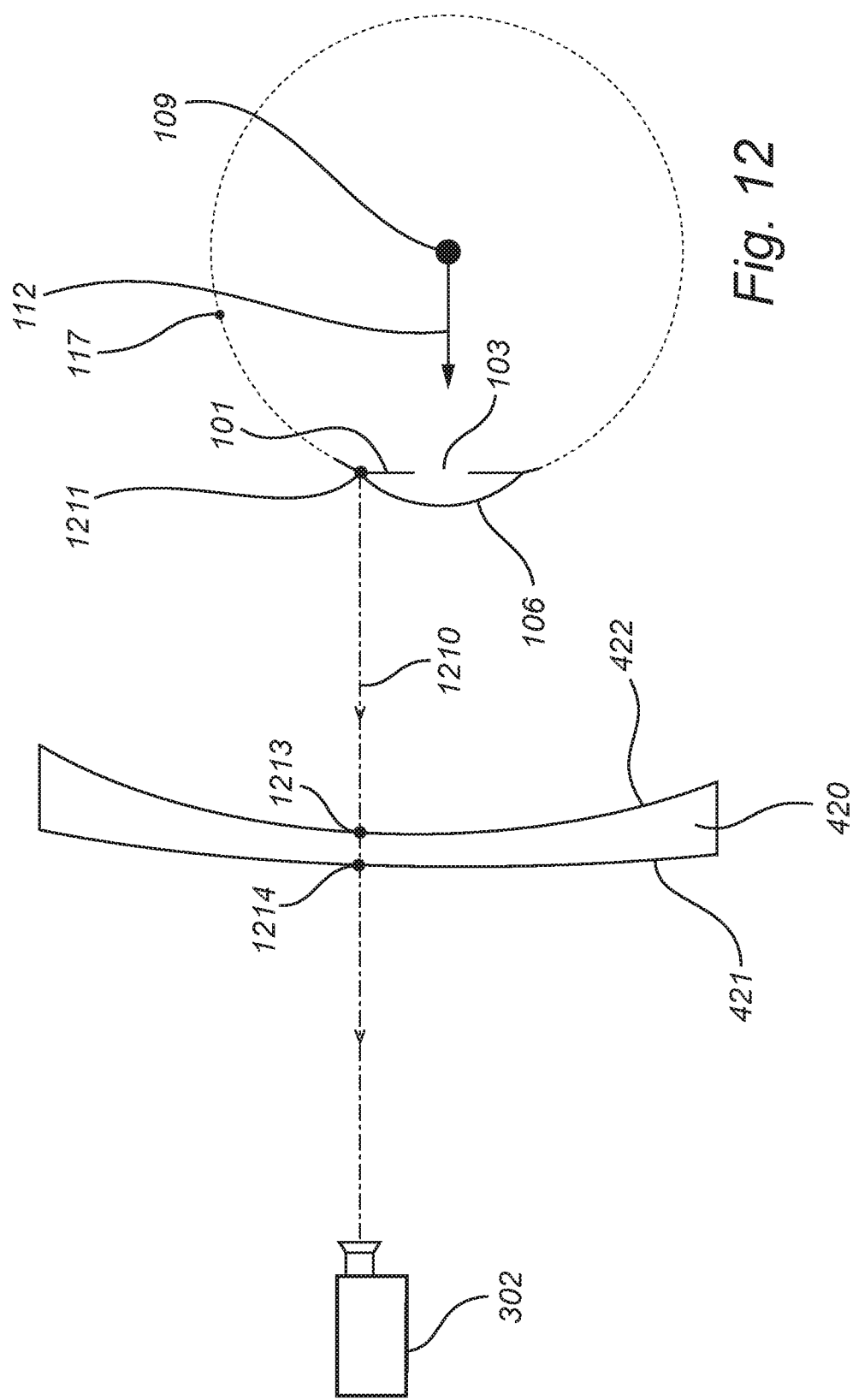
FIG. 12 is a schematic overview of a path for light travelling from an edge of an iris of an eye to a camera.
Figure 13:
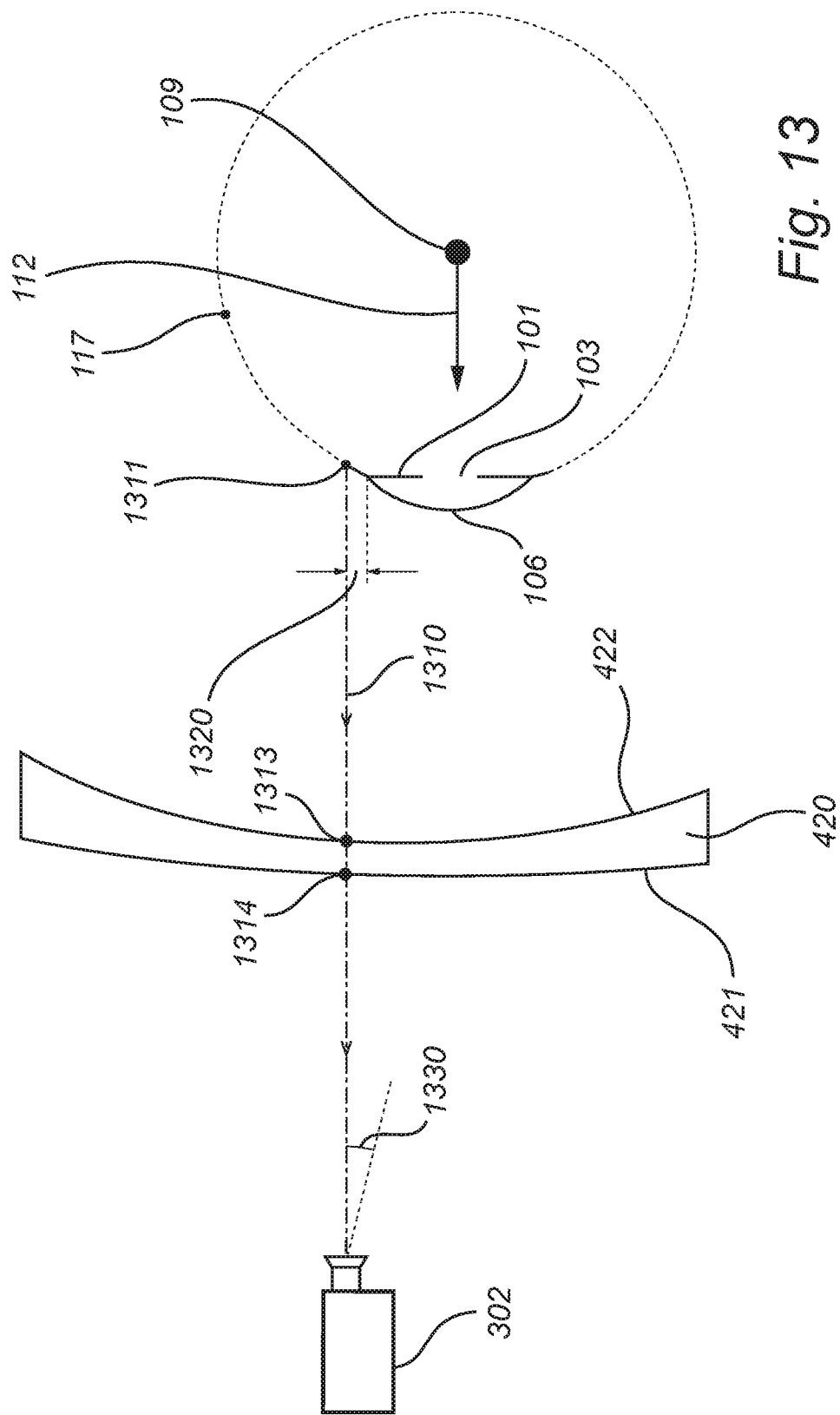
FIG. 13 is a schematic overview of a path for light travelling from a sclera of an eye to a camera.

FIG. 12 is a schematic overview of a path 1210 for light travelling from a point 1211 along the edge 102 (the edge 102 is shown in FIG. 1) of the iris 101 of the eye 100 to the camera 302. In the example shown in FIG. 12, the user wears glasses 420. The example path 1210 shown in FIG. 12 leaves a point 1211 along the edge 102 of the iris 101, which is located at the corneal limbus where the cornea 106 meets the sclera 117. Hence, if the point 1211 is located along the inside of the edge 102 of the iris 101 as perceived in images of the eye 100 (such as in FIG. 1), then the path 1210 would pass through at least a portion of the cornea 106, and may potentially be refracted when it leaves the cornea 106. If the point 1211 is located along the outside of the edge 102 of the iris 101 as perceived images of the eye 100 (such as in FIG. 1), then the path 1210 would potentially start at the sclera 117 (as shown in FIG. 13), and may therefore potentially not pass through the cornea 106 at all. After the light has left the eye 100, the light reaches the second surface 422 of the glasses 420 at a point 1213. The light is refracted at the point 1213. The light then reaches the first surface 421 of the glasses 420 at a point 1214 and is refracted there again. The light then reaches the camera 302. Depending where the eye 100 is located in space (which may be defined via the position of the center of the eye 109), and how the eye 100 is oriented in space (which may be defined via the optical axis 112), the point 1211 along the iris edge 102 (which may be regarded as the origin of the light path 1210) may appear at different positions in images of the eye 100 captured by the camera 302. Hence, iris edge positions may be predicted for different positions and orientations of the eye 100, and may be compared with an observed iris edge in an image captured by the camera 302, as part of a method for determining the position and orientation of the eye 100.

FIG. 9 shows an iris edge 904 detected in an image 900 captured by the camera 302, and an iris edge position 905 predicted using the light path 1210 in FIG. 12. The predicted iris edge position 905 is located a distance 906 away from the detected iris edge 904. If the position and orientation of the eye 100 employed for a light path 1210 between the iris edge 102 and the camera 302 is correct, this distance 906 should be relatively small. Although the distance 906 may in theory be zero, noise may affect the accuracy of the detected iris edge 904, and approximations and/or simplifications may be employed when computing how the light would be refracted along the path 1210, which may affect the accuracy of the predicted iris edge position 905.

FIG. 13 is a schematic overview of a path 1310 for light travelling from the sclera 117 to the camera 302. The path 1310 is close to the iris edge 102, but misses it by a distance 1320 and instead originates at the sclera 117. The light path 1310 does not pass through the cornea 106 but is refracted at points 1313 and 1314 at the surfaces 422 and 421 of the glasses 420 before reaching the camera 302. The light path 1310 reaches the camera 302 at a certain direction, which is illustrated herein by the angle 1330. Although only the angle 1330 is shown in FIG. 12, it will be appreciated that a direction in 3D space may be defined via two separate angles (for example by the two angles in a spherical coordinate system). By appropriately selecting the direction at which the path 1310 is to reach the camera 302, one may decrease the distance 1320, or even find a path that originates at the iris edge 102, as in FIG. 12. Although the path 1310 does not actually originate at the iris edge 102, a projection into the camera 302 may still be computed, so as to obtain a predicted position for the path 1310, in analogy with the predicted iris edge position 905 of the path 1210 shown in FIG. 9.

In analogy with FIG. 11 (where the light path 1110 comes from the pupil edge 104), a light path from the iris edge 102 may also miss the camera 302, depending on in which direction it leaves the iris edge 102.

Optimization

The light paths described above with reference to FIGS. 4-13 may be employed for gaze tracking. More specifically, an optimization problem may be formulated for determining the true position and orientation of the eye 100 in space. As described above with reference to FIGS. 5 and 9, a predicted feature should be located close to a corresponding detected feature if the position 109 and the orientation 112 of the eye 100 is correct. An objective function (or cost function) may therefore be formulated based on differences between predicted features and corresponding detected features. More specifically, let p denote the position 109 of the eye 100 in space, let o denote the orientation 112 of the eye 100 in space, let lg denote the direction that the glint light path reaches the camera 302, and let le denote the direction in which the light path from the pupil edge 104 (or from the iris edge 102) reaches the camera 302. Then the position p and orientation o of the eye 100 in space may be obtained by solving the following optimization problem:

$$(p,o,lg,le) = \mathrm{argmin}_{(p,o,lg,le)} \Sigma_{n=1}^{N} \mathrm{loss}(\mathrm{image\_feature}_n, \mathrm{predicted\_feature}_n(p,o,lg,le)) \quad (1)$$

subjected to the condition:

$$g_k(p,o,lg,le)=0, \text{ for } k=1,\ldots,K \quad (2)$$

In the above equation 1, the N features image_feature$_n$ are detected features, and the N features predicted_feature$_n$(p, o, lg, le) are predicted features. These detected and predicted features include one or more glints, one or more points along the pupil edge 104 (or one or more points along the iris edge 102). The function "loss" is a loss function such that the value of loss(A, B) increases as the difference between the points A and B increases. The K conditions $g_k$(p, o, lg, le)=0 correspond to requiring that the light paths start at the correct position (such as at the illuminator 301, at the pupil edge 104, or at the iris edge 102) and reach the respective camera 302.

The loss function "loss" employed for the detected and predicted corneal reflections (or glints) may for example be the squared distance, or the L1, L2 or Huber loss.

Points along the pupil edge 104 may be employed to obtain a predicted pupil center position and a detected pupil center position. The loss function "loss" employed for the detected and predicted pupil center may for example be the squared distance, or the L1, L2 or Huber loss.

The loss function "loss" employed for the detected and predicted iris radius may for example be the squared distance, or the L1, L2 or Huber loss.

The physicality constraints in the above equation 2 require that the distance between the light ray and the illuminator 301 (and the light ray and the camera 302) is numerically zero. If, however, no such solution can be found, the squared shortest distance could be is used. For example, the hard constraints in equation 2 may be replaced with a relaxed optimization problem. In this case, the constraint terms are added to the function to be minimized in equation 1, multiplied by a large constant.

The optimization problem defined by the equations 1 and 2 (or a relaxed version thereof) may be solved numerically. Sequential quadratic programming may for example be employed to solve the optimization problem.

The pupil 103 may change radius 118 relatively quickly, so the pupil radius 118 may not be known in advance. If the above optimization problem is supposed to involve a position along the pupil edge 104 as a predicted feature, then a light path from the pupil edge 104 to the camera 302 may be estimated (as in FIG. 8) based on a preliminary value (or initial guess) for the pupil radius 104. In other words, the pupil radius 104 could also be treated as an unknown in the optimization problem. Denoting the pupil 104 radius by r, the optimization problem could be formulated as:

$$(p,o,lg,le,r) = \mathrm{argmin}_{(p,o,lg,le,r)} \Sigma_{n=1}^{N} \mathrm{loss}(\mathrm{image\_feature}_n, \mathrm{predicted\_feature}_n(p,o,lg,le,r)) \quad (3)$$

subjected to the condition:

$$g_n(p,o,lg,le,r)=0, \text{ for } n=1,\ldots,N \quad (4)$$

The optimization problem defined by the equations 3 and 4 (or a relaxed version thereof) may be solved numerically. Sequential quadratic programming may for example be employed to solve the optimization problem.

Initial Guess for the Optimization

Most solvers need an initial guess. A PCCR gaze tracker may for example be employed to obtain initial guesses for the position 109 of the eye 100 and the orientation 112 of the eye 100.

The initial direction for a light ray from a point at the pupil edge 104 or the iris edge 102 may be selected such that that the ray goes directly to the camera 302.

The initial direction for light rays for glints may selected using the glints detected in the image. The initial direction for light from the illuminator may for example be selected directly towards the cornea.

Example Embodiments

Figure 14:
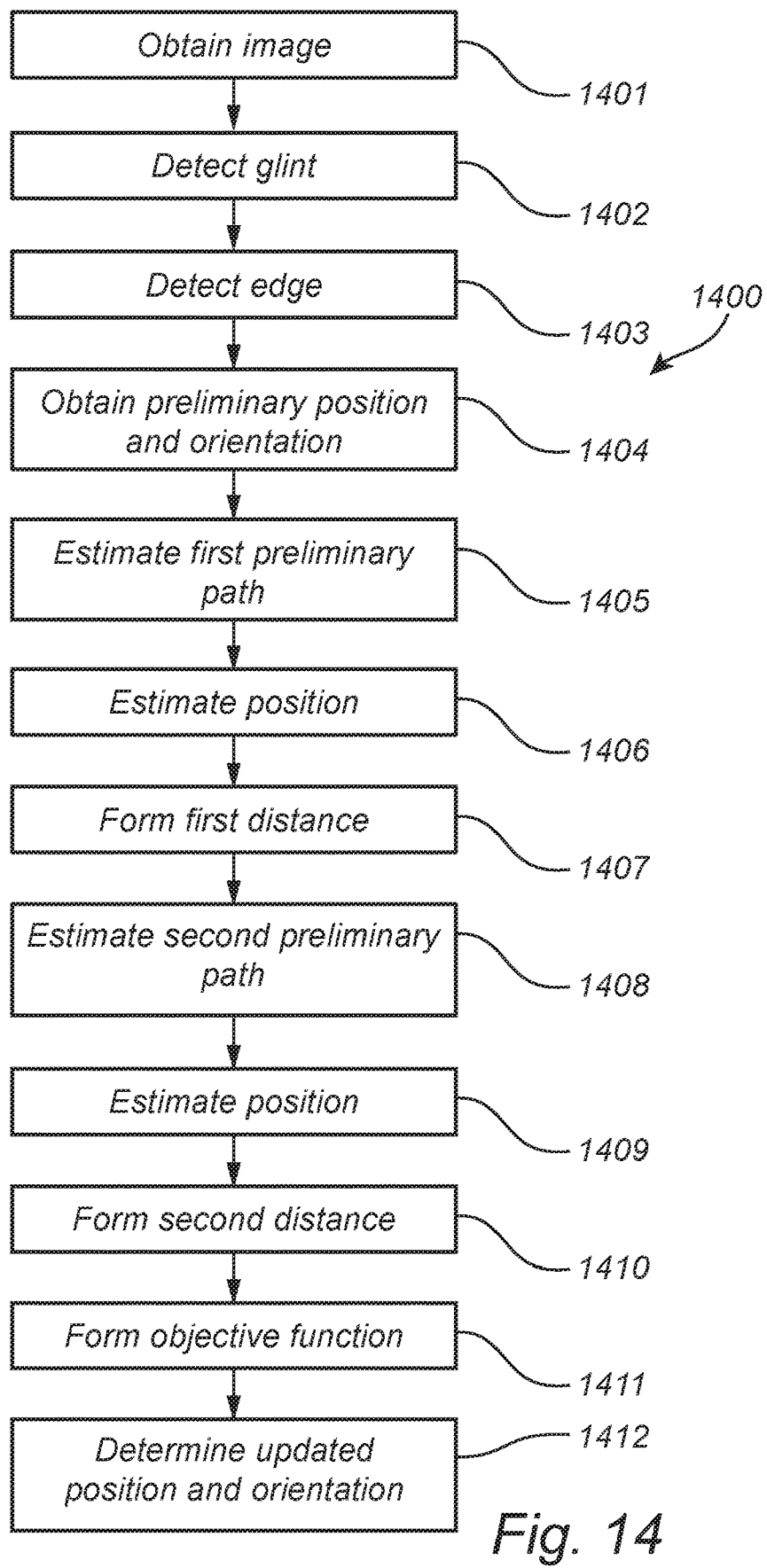
FIG. 14 is a flow chart of a gaze tracking method, according to an embodiment.

FIG. 14. is a flow chart of a gaze tracking method 1400, according to an embodiment. The method 1400 may for example be performed by the gaze tracking system 300, or by the processing circuitry 304 of the gaze tracking system 300. The method 1400 will be described with reference to FIGS. 1-14.

The method 1400 comprises obtaining 1401 (or receiving) one or more images of an eye 100. An image 500 of the one or more images has been captured by a camera at a time instance (or at a point in time) while the eye 100 was illuminated by an illuminator 301. The image 500 captured by the camera shows a first reflection 501 of the illuminator 301 at a cornea 106 of the eye 100. An image 900 of the one or more images has been captured by a camera at the same time instance (or at the same point in time) and shows at least a portion of an edge. The edge is an edge 104 of a pupil 103 of the eye 100 (the pupil edge is denoted by 901 in FIG. 9), or an edge 102 of an iris 101 of the eye 100 (the iris edge is denoted by 904 in FIG. 9).

The image 500 showing a first reflection 501 of the illuminator 301 at a cornea 106 of the eye 100 may for example coincide with the image 900 showing at least a portion of the edge (so the features shown in FIG. 5 and FIG. 9 could all be present in the same image). However, in other example implementations, the image 500 showing a first reflection 501 of the illuminator 301 at a cornea 106 of the eye 100 may be distinct from the image 900 showing at least a portion of the edge. The image 500 showing a first reflection 501 of the illuminator 301 at a cornea 106 of the eye 100 may for example be captured by a different camera than the image 900 showing at least a portion of the edge. In other words, the system 300 may comprise multiple cameras 302, where one camera 302 captures the image 500 and another camera captures the image 900. The images 500 and 900 may be captured simultaneously, so that the position and orientation of the eye 100 in space is the same for both of the images 500 and 900.

The one or more images may for example be digital images. The one or more images may for example be obtained in the form of snap shots, or as part of a video sequence. The images may for example be received from the camera(s) 302, either directly from the camera(s) 302 or indirectly from the camera(s) 302 (for example via one or more other components of the system 300).

The method 1400 comprises detecting 1402 a position 501 of the first reflection (or glint) in the image 500 showing the first reflection. The position 501 may for example be detected via image analysis, such as digital image analysis. The position 501 may for example be at the center of the first reflection in the image 500 showing the first reflection.

The method 1400 comprises detecting 1403 at least a portion of the edge in the image 900 showing at least a portion of the edge. The detected edge may for example be the pupil edge 901 or the iris edge 904. The edge (or a portion thereof) may for example be detected via image analysis, such as digital image analysis. It will be appreciated that part of the pupil edge 904 or of the iris edge 902 may for example not be visible in the image 500, and may therefore not be detected.

The method 1400 comprises obtaining 1404 a preliminary position 109 of the eye 100 in space and a preliminary orientation 112 of the eye 100 in space.

The preliminary position 109 may for example be received, or it may be determined. It will be appreciated that the preliminary position 109 need not necessarily be a true or actual position of eye 100. The preliminary position 109 may be a potential position which is considered in the method 1400 while looking for the true position of eye 100 in space. The preliminary position 109 may for example be an initial guess or starting point.

The preliminary orientation 112 may for example be received, or it may be determined. It will be appreciated that the preliminary orientation 112 need not necessarily be a true or actual orientation of eye 100. The preliminary orientation 112 may be a potential orientation which is considered in the method 1400 while looking for the true orientation of eye 100 in space. The preliminary orientation 112 may for example be an initial guess or starting point.

The method 1400 comprises estimating 1405, based on the preliminary position 109 of the eye 100 and the preliminary orientation 112 of the eye 100, a first preliminary path for light travelling towards the camera 302 via a reflection at the cornea 106.

The first preliminary path may for example be the example path 410 described above with reference to FIG. 4, where the light path 410 goes from the illuminator 301 to the camera 302, via a reflection at the cornea 106. If the user wears glasses 420, as in FIG. 4, then refraction at the glasses 420 may be taken into account when estimating 1405 the first preliminary path. However, the effect of the glasses 420 could be disregarded (for example to simplify computations) in case it is not considered necessary for adequate gaze tracking performance. If the user does not wear glasses, there is no need to take such refraction into account.

The first preliminary path may for example be the example path 610 described above with reference to FIG. 6. In other words, the first preliminary path may reach the camera 302 but need not start at the illuminator 301. If the optimization problem in equations 1 and 2 is to be solved with the strict condition in equation 2, then the strict condition in equation 2 requires the path to start at the illuminator 302 and to reach the camera 302. If, however, the optimization problem in equations 1 and 2 is solved via Lagrange relaxation, then the condition in equation 2 need not be strictly enforced, and paths such as the example path 610 may also be of interest.

The first preliminary path may for example be the example path 710 described above with reference to FIG. 7. In other words, the first preliminary path may start at the illuminator 301 but may not actually reach into the camera 302. If the optimization problem in equations 1 and 2 is to be solved with the strict condition in equation 2, then the strict condition in equation 2 requires the path to start at the illuminator 301 and to reach the camera 302. If, however, the optimization problem in equations 1 and 2 is solved via Lagrange relaxation, then the condition in equation 2 need not be strictly enforced, and paths such as the example path 710 may also be of interest.

During the rest of the description of the method 1400, the first preliminary path will be exemplified by the example path 410 from FIG. 4, but it will be appreciated that the first preliminary path may just as well be of types described above with reference to FIGS. 6 and 7.

The method 1400 comprises estimating 1406 (or predicting) a position 502 where the reflection from the first preliminary path 410 would appear in images of the eye 100 captured by the camera 302 by which the image 500 showing the first reflection was captured. The position 502 where the reflection from the first preliminary path 410 would appear may for example be estimated or predicted by applying a projection into the camera 302. If the user wears glasses 420, the last refraction point 415 at the glasses 420 may for example be projected into the camera 302. If the user does not wear glasses 420, the reflection point 413 at the cornea 106 may for example be projected into the camera 302.

The method 1400 comprises forming 1407 a first distance 503 between the detected position 501 of the first reflection in the image 500 showing the first reflection and the estimated position 502 where the reflection from the first preliminary path 410 would appear. The first distance 503 may for example be measured in the image 500 captured by the camera 302.

The method 1400 comprises estimating 1408, based on the preliminary position 109 of the eye 100 and the preliminary orientation 112 of the eye 100, a second preliminary path for light travelling through at least a portion of the cornea 106 of the eye 100 towards the camera 302, or a second preliminary path for light travelling from a sclera 117 of the eye 100 towards the camera 302.

The second preliminary path may for example be the light path 810 described above with reference to FIG. 8, where light path 810 goes from the pupil edge 104, through the cornea 106, to the camera 302. If the user wears glasses 420, as in FIG. 8, then refraction at the glasses 420 may be taken into account when estimating 1408 the second preliminary path. However, the effect of the glasses 420 could be disregarded (for example to simplify computations) in case it is not considered necessary for adequate gaze tracking performance. If the user does not wear glasses, there is no need to take such refraction into account. As shown in FIG. 8, the light path 810 is refracted at a point 812 at the cornea 106. This effect may for example be taken into account when estimating the second preliminary path. However, the effect of the refraction at the cornea 106 could be disregarded (for example to simplify computations) in case it is not considered necessary for adequate gaze tracking performance.

The second preliminary path may for example be the light path 1010 described above with reference to FIG. 10. In other words, the second preliminary path may reach the camera 302 but need not start at the pupil edge 104. If the optimization problem in equations 1 and 2 is to be solved with the strict condition in equation 2, then the strict condition in equation 2 requires the path to start at the pupil edge 104 and to reach the camera 302. If, however, the optimization problem in equations 1 and 2 is solved via Lagrange relaxation, then the condition in equation 2 need not be strictly enforced, and paths such as the example path 1010 may also be of interest.

The second preliminary path may for example be the light path 1110 described above with reference to FIG. 11. In other words, the second preliminary path may start at the pupil edge 104, but need not reach into the camera 302. If the optimization problem in equations 1 and 2 is to be solved with the strict condition in equation 2, then the strict condition in equation 2 requires the path to start at the pupil edge 104 and to reach the camera 302. If, however, the optimization problem in equations 1 and 2 is solved via Lagrange relaxation, then the condition in equation 2 need not be strictly enforced, and paths such as the example path 1110 may also be of interest.

The second preliminary path may for example be the light path 1210 described above with reference to FIG. 12. In other words, the second preliminary path 1210 may go from the iris edge 102, pass through a portion of the cornea 106, and reach into the camera 302. As described above, taking the presence of glasses 420 into account is optimal.

The second preliminary path may for example be the light path 1310, described above with reference to FIG. 13. In other words, the second preliminary path may reach the camera 302 but need not start at the iris edge 102. As shown in FIG. 13, the light path 1310 may for example start at the sclera 117. If the optimization problem in equations 1 and 2 is to be solved with the strict condition in equation 2, then the strict condition in equation 2 requires the path to start at the iris edge 102 and to reach the camera 302. If, however, the optimization problem in equations 1 and 2 is solved via Lagrange relaxation, then the condition in equation 2 need not be strictly enforced, and paths such as the example path 1310 may also be of interest.

The second preliminary path may for example start at the iris edge 102 but may not reach into the camera 302. If the optimization problem in equations 1 and 2 is to be solved with the strict condition in equation 2, then the strict condition in equation 2 requires the path to start at the iris edge 102 and to reach the camera 302. If, however, the optimization problem in equations 1 and 2 is solved via Lagrange relaxation, then the condition in equation 2 need not be strictly enforced, and paths such as the example path starting at the iris edge 102 but not reaching into the camera 302 may also be of interest.

During the rest of the description of the method 1400, the second preliminary path will be exemplified by the example path 810 from FIG. 8, but it will be appreciated that the second preliminary path may for example just as well be of types described above with reference to FIGS. 10-13.

The method 1400 comprises estimating 1409 (or predicting) a position 902 where the second preliminary path 810 would appear to originate (or a position where it would appear to come from) in images of the eye 100 captured by the camera 302 by which the image 900 showing at least a portion of the edge was captured. The position 902 where the second preliminary path 810 would appear to originate may for example be estimated or predicted by applying a projection into the camera 302. If the user wears glasses 420, the last refraction point 814 at the glasses 420 may for example be projected into the camera 302. If the user does not wear glasses 420, the refraction point 812 at the cornea 106 may for example be projected into the camera 302.

The method comprises forming 1410 a second distance 903 between the edge 902 and the estimated (or predicted) position 902 where the second preliminary path 810 would appear to originate. The second distance 903 may for example be measured in the image 900 captured by the camera 302. If only a portion of the edge 902 has been detected 1403 in the image 900 (this may for example happen if part of the edge 902 is not visible in the image), positions of the rest of the edge 902 may for example be estimated based on an expected shape of the edge 902. The expected shape may for example be obtained or determined based on a model of the pupil 103. An ellipse may for example be fitted to those parts of the pupil edge 904 that are detected in the image 900.

The method 1400 comprises forming 1411 an objective function based on at least the first distance 503 and the second distance 903. The objective function may for example be referred to as an evaluation function, or an assessment function. The objective function may for example be a loss function or a cost function.

The objective function may for example be adapted to increase when the first distance 503 increases, and to increase when the second distance 903 increases. The method 1400 may for example strive to find a position and orientation of the eye 100 in space, so that the objective function is reduced or minimized (i.e. so that a value of the objective function is as small as possible). The function that is to be minimized in equation 1 is an example of such an objective function.

The objective function may for example be adapted to decrease (or being reduced) when the first distance 503 increases, and to decrease (or being reduced) when the second distance 903 increases. The method 1400 may for example strive to find a position and orientation of the eye 100 in space, so that the objective function is increased or maximized (i.e. so that a value of the objective function is as large as possible). If the function that is to be minimized in equation 1 is multiplied by −1, then it may be employed as an example of such an objective function that is to be maximized.

The method 1400 comprises determining 1412, using the objective function, an updated (or new) position of the eye 100 in space and/or an updated (or new) orientation of the eye 100 in space. A new position of the eye 100 in space and/or a new orientation of the eye 100 in space may for example be determined such that the value of the objective function is decreased (or minimized), or such that the value of the objective function is increased (or maximized).

The method 1400 may for example repeat the steps 1405-1412 for the updated position and/or orientation of the eye 100 until an extremum/optimum (such as a minimum or maximum) of the objective function has been reached, or until a value of the objective function is below a threshold (or exceeds a threshold). The method 1400 may for example employ an optimization method such as a gradient descent method.

The final position and orientation of the eye 100 obtained in this way may for example estimate the true position of the eye 100 and the true orientation of the eye 100, an may therefore be employed to estimate a gaze point and/or a gaze direction of the eye 100.

The steps 1409-1412 have been described above in a context where the pupil edge 901 is employed as the detected feature in the image 900. As describe above with reference to FIGS. 9, 12 and 13, the iris edge 904 may for example be employed instead. Hence, the second preliminary path may for example be the path 1210 in FIG. 12, and the step of forming 1410 a second distance may form a distance 906 between the edge 904 of the iris and the estimated position 905 where the second preliminary path 1210 would appear to originate. In such an example implementation, the objective function may be formed at the step 1411 based on at least the first distance 503 and the second distance 906.

According to some embodiments, the method 1400 may comprise estimating a gaze direction and/or a gaze point (such as the gaze point 115 in FIG. 2) based on the updated position and/or updated orientation of the eye 100 determined at the step 1412.

As described above with reference to FIG. 4, the user may wear glasses 420. Hence, according to an embodiment, the step 1405 of estimating the first preliminary path 410 may comprise estimating refraction of light at one or more surfaces of the glasses 1420. Similarly, according to an embodiment, the step 1408 of estimating the second preliminary path 810 may comprise estimating refraction of light at one or more surfaces of the glasses 420.

It will be appreciated that the glasses 420 depicted in FIG. 4 are only intended as an example, and that many other types and/or shapes of glasses may be envisaged. The glasses 420 may for example be modeled as a lens with two spherical surfaces 421 and 422. Different glasses may be modeled by selecting whether the lens is concave or convex, and by selecting the radii of the surfaces. Glasses 420 with non-spherical surfaces may also be modeled.

In an embodiment, the user provides the radii of the surfaces of the glasses 420, the thickness of the glasses 420 and the refractive index of the glasses 420.

In an embodiment, the user provides the diopters of the glasses 420, and then the radii, thickness and refractive index are looked up in a table.

In an embodiment, refraction at the glasses 420 is only modeled (or estimated) for some light paths.

In an embodiment, refraction at the glasses 420 is only modeled (or estimated) in the forward or backwards pass of a light ray reflected at the cornea 106.

Figure 15:
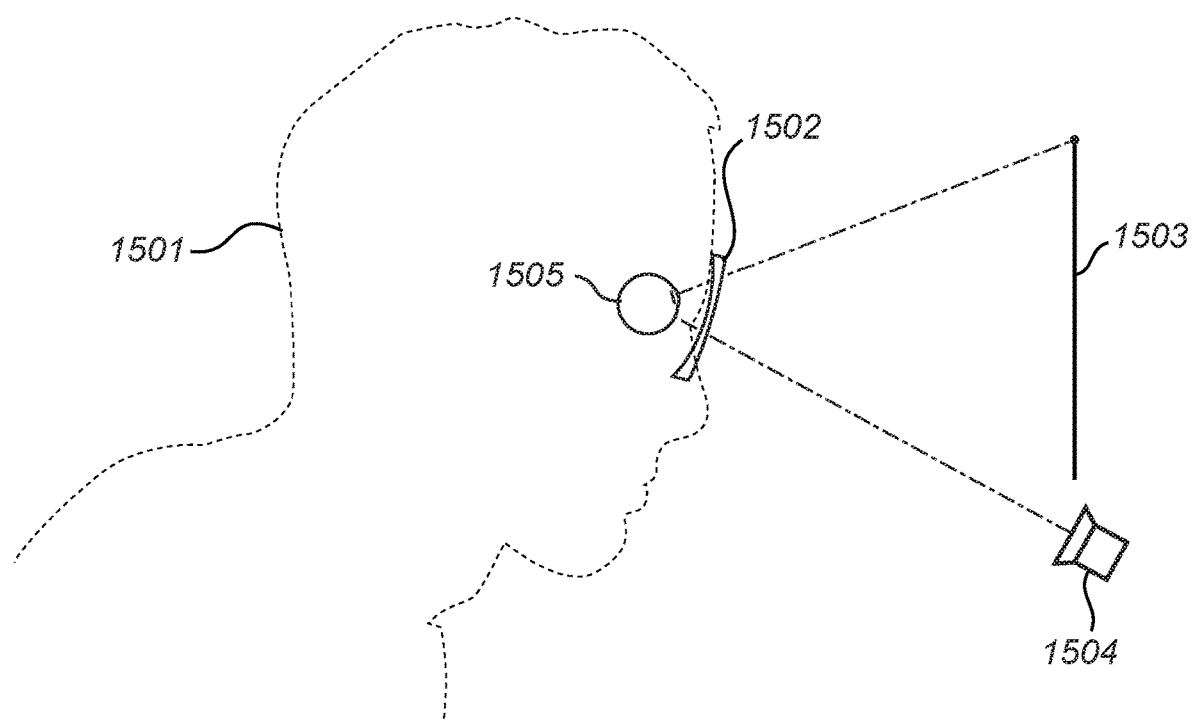
FIGS. 15 and 16 illustrate that the head pose of a user wearing glasses may affect how light paths interact with the glasses.
Figure 16:
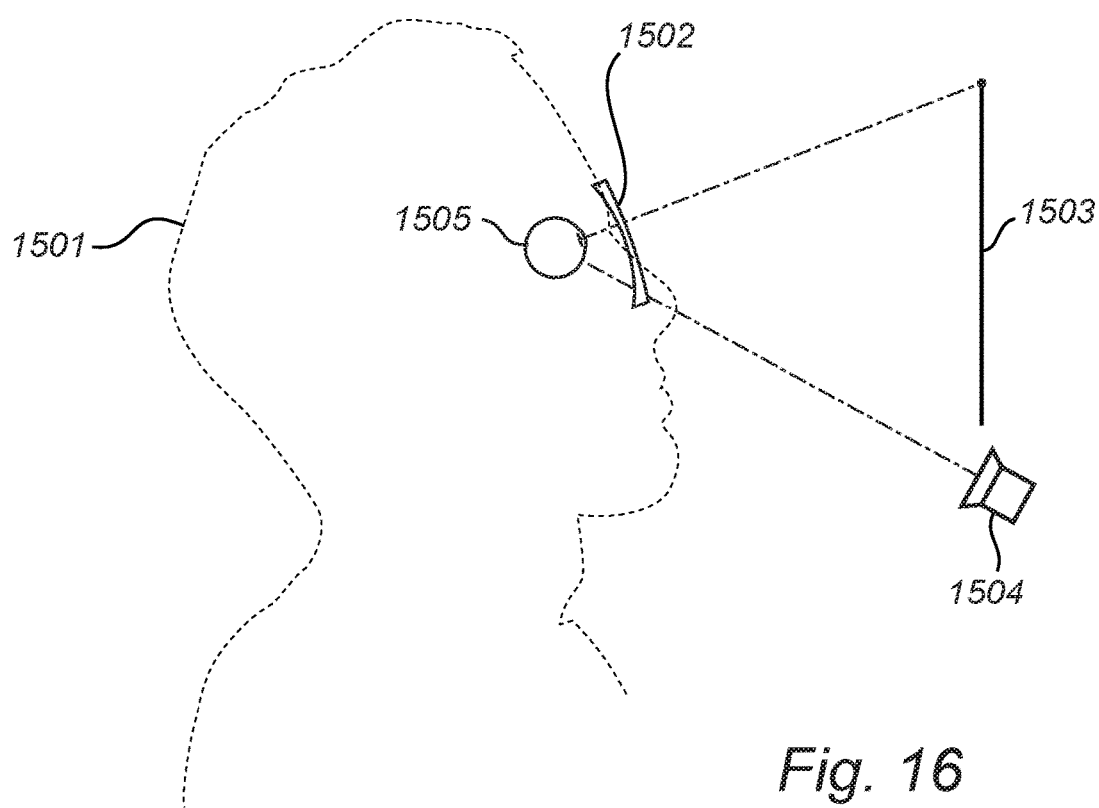

The position and/or orientation of the glasses 420 typically affect how the light is refracted. For example, the angle at which light reaches a surface of the glasses 420 affects how the light is refracted. This is illustrated in FIGS. 15 and 16. The glasses 420 may also be positioned such that the user looks through the glasses 420 towards a display, but the camera 302 captures images from an angle such that light rays from the eye 100 to the camera 302 do not pass through the glasses 420.

FIG. 15 shows a user 1501 wearing glasses 1502. A display 1503 is arranged in front of the user 1501 and a camera 1504 below the display 1503 captures images of the user's face, for gaze tracking purposes. The user's head is directed towards the camera 1504, but the user 1501 is looking at region at the top of the display 1503. The camera 1504 sees the user's eye 1505 through the glasses 1502 from a direction more or less straight into the glasses 1502.

In FIG. 16, the head of the user 1501 is tilted back so that it is directed towards the top of the display 1503. With this head pose, the camera 1504 sees the user's eye through the glasses 1502 at a different angle relative to the glasses 1502 than in FIG. 15.

Since light rays between the eye 1505 and the camera 1504 in FIG. 16 would meet the surfaces of the glasses 1502 at a different angle than corresponding light rays in FIG. 15, the refraction would be different, and this would affect how features of the eye 1505 appear in images captured by the camera 1504. When the user 1501 tilts his/her head, the glasses 1502 will be angled relative to the camera 1504. Roughly speaking, this tilt will make things look shorter in the direction of the tilt. This effect may preferable be taken into account when performing gaze tracking.

Hence, according to an embodiment, the method 1400 described above with reference to FIG. 14 comprises obtaining a position and/or orientation of glasses 420 worn by the user. In the present embodiment, refraction at one or more surfaces of the glasses 420 is estimated based on the obtained position and/or orientation. The refraction may for example be estimated (or computed) as part of the step 1405 of estimating the first preliminary path, and/or of the step 1408 of estimating the second preliminary path.

In an embodiment, the user provides the position of the glasses 420.

In an embodiment, the glasses 420 are assumed to be in a fixed position relative to the camera 302.

In an embodiment, the glasses 420 are assumed to be in a fixed position relative to the user's eyes.

As described above with reference to FIGS. 15-16, the position and/or orientation of the glasses typically changes when the head of the user moves or rotates. Hence, according to some embodiments, a head pose of the user may be monitored, and the position and/or orientation of the glasses 420 may be obtained (or determined) based on a head pose. The monitoring may for example include monitoring of the position of the head in space, and the rotation/pitch of the head. The glasses 420 may for example be assumed to be arranged at a fixed position and orientation relative to the user's head.

The head pose may for example be monitored via sensors mounted at the head of the user (for example in a head-mounted device), or via an optical sensor and image analysis.

Figure 17:
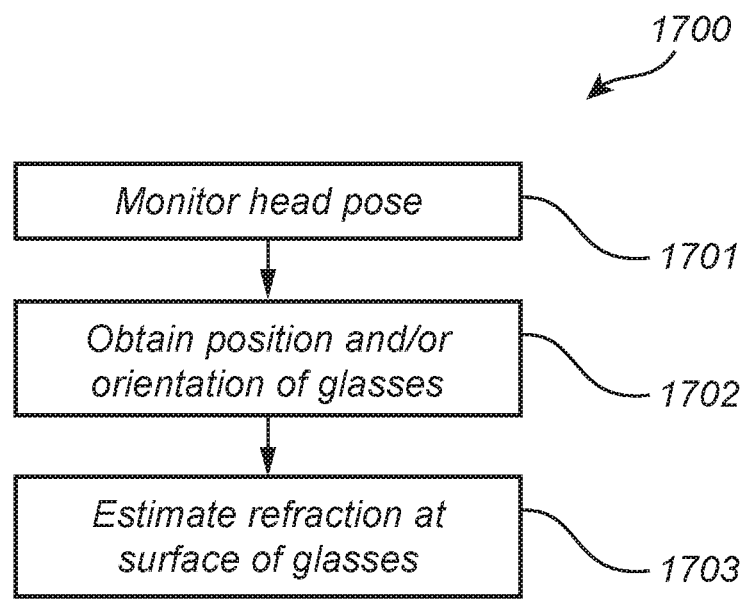
FIG. 17 is a flow chart of a scheme for estimating refraction at glasses, which may be employed as part of the method in FIG. 14, according to an embodiment.

FIG. 17 is a flow chart of a scheme 1700 for estimating refraction of light at glasses 420, in accordance with the above observations. The scheme 1700 may for example be employed as part of the method 1400 described above with reference to FIG. 14. The scheme 1500 comprises:
- monitoring 1701 a head pose of the user;
  - obtaining 1702 a position and/or orientation of the glasses 420 worn by the user based on the head pose, and
  - estimating 1703 refraction at one or more surfaces of the glasses 420 based on the obtained position and/or orientation of the glasses 420.

The first preliminary path determined at the step 1405 (described above with reference to FIG. 14) includes a reflection at the cornea 106 of the eye 100. Traditionally, the cornea 106 is modeled as a spherical surface. While a reflection at a spherical surface may be relatively easy to compute, gaze tracking performance may be improved by taking into account the fact that the cornea 106 is typically not perfectly spherical.

Figure 18:
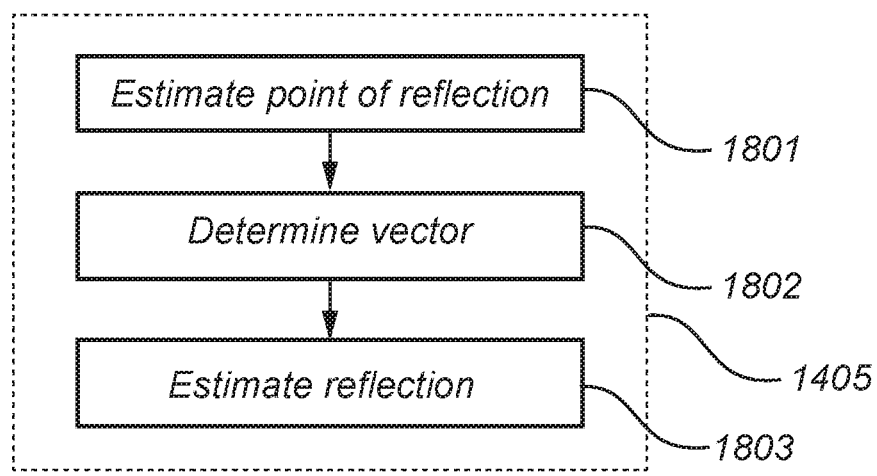
FIG. 18 is a flow chart of a scheme for estimating reflection at the cornea, which may be employed as part of the method in FIG. 14, according to an embodiment.

FIG. 18 is a flow chart of a scheme for estimating reflection at the cornea 106. This scheme may be employed as part of the step 1405 of estimating the first preliminary path in the method 1400 described above with reference to FIG. 14. Hence, according to an embodiment, the step 1405 of estimating the first preliminary path comprises:
- estimating 1801 a point 413 of reflection (see FIG. 4) at the cornea 106;
- determining 1802 a vector 440 using a mapping (or function), wherein the mapping is adapted to map points at the cornea 106 to respective vectors; and
- estimating 1803 a reflection at the point 413 of reflection using the determined vector 440 as a normal vector.

In other words, a mapping or function is employed to determine the vector which is to be employed as a normal vector when estimating how the reflection at the cornea 106 will be. The reflection may for example be computed via the law of reflection.

The mapping may for example be employed to handle non-spherical cornea shapes, such as in the case of astigmatism. If the user wears a contact lens at the cornea 106, this may affect the shape of the surface at which light from the illuminator 301 is reflected. The mapping may for example be employed to handle reflection at such surfaces.

The mapping may for example be a normal mapping. Normal mappings are for example employed in computer graphics to simulate lighting of bumps and dents. Normal mappings are described further below in a separate section.

According to an embodiment, the step of estimating 1801 a point 413 of reflection comprises determining an intersection between a line and a surface (for example a spherical surface). In the present embodiment, the vector determined 1802 using the mapping forms an angle relative to a normal vector of the surface at the point of intersection. In other words, although a surface is employed to estimate 1801 the point 413 of reflection, the normal vector of that surface at the point 413 of reflection is not employed for estimating the reflection. Instead, the mapping (for example a normal mapping) is employed to determine 1802 a different vector to be employed as a normal vector when estimating 1803 the reflection. It will be appreciated that the angle formed between the vector determined 1802 using the mapping and the normal vector of the surface is non-zero.

If a too complicated shape is employed in a cornea model, it may be difficult to determine the point 413 of reflection (which may be approximated as the point of intersection between the light ray and the cornea model). The cornea model may instead employ a relatively simple shape (such as a spherical surface), accompanied by a normal mapping which assigns normal vectors differing from the normal vectors of the simple shape. Thereby, the point 413 or reflection may be easily determined, and an appropriate normal vector may be assigned to take into account the fact that reflections at the cornea 106 may be more complicated than reflections at a simple surface such as a sphere. As mentioned above, the surface employed in the cornea model may for example be a spherical surface.

According to an embodiment, the first preliminary path estimated at the step 1405 of the method 1400 may be a preliminary path for light travelling from the illuminator 301 to the camera 302 via a reflection at the cornea 106, as exemplified by the path 410 in FIG. 4.

As described above with reference to FIG. 6, light paths 610 which do not originate at the illuminator 302 may also be considered in the method 1400. Hence, according to an embodiment, the step 1405 of estimating the first preliminary path comprises:
- obtaining a preliminary direction for light to reach the camera 302; and
- estimating the first preliminary path as a preliminary path 610 for light reaching the camera 302 in the preliminary direction via a reflection at the cornea 106.

In the present embodiment, the method 1400 comprises determining, using the objective function, an updated position of the eye 100 in space and/or an updated orientation of the eye 100 in space and/or an updated direction for light to reach the camera 302. This determination is performed subjected to a condition that the position 109 of the eye 100, the orientation of the eye 112, and the direction for light to reach the camera 302 correspond to a path 410 (see FIG. 4) for light travelling from the illuminator 301 to the camera 302 via a reflection at the cornea 106. In other words, although the first preliminary path 610 may not originate at the illuminator 301, an updated position of the eye 100 in space and/or an updated orientation of the eye 100 in space and/or an updated direction for light to reach the camera 302 is determined such that a light path associated with these updated parameters does originate at the illuminator 301. This determination may for example be part of the step 1412 of determining an updated position and/or orientation of the eye 100 in space. It will be appreciated that in at least some cases, it may be sufficient to update only one of the position 109 of the eye 100 in space, the orientation 112 of the eye 100 in space, and the direction for light to reach the camera 302, to find a light path that goes from the illuminator 301 to the camera 302 via reflection at the cornea 106 (like the light path 410 in FIG. 4). In other words, there may be no need to update all three of these to find such a light path.

According to an embodiment, the step 1405 of estimating the first preliminary path in the method 1400 comprises:
- obtaining a preliminary direction for light to reach the camera 302;
- estimating a preliminary path 610 (see FIG. 6) for light reaching the camera 302 in the preliminary direction via a reflection at the cornea 106;
- forming a further distance 620 between the preliminary path 610 and the illuminator 301;

determining, based on the further distance 620, an updated direction for light to reach the camera 302; and estimating the first preliminary path as a path 410 (see FIG. 4) for light reaching the camera 302 in the updated direction via a reflection at the cornea 106.

In other words, the first preliminary path may be determined by trying different directions for light to reach the camera 302, and to use the distance 620 as a measure of how close the path is to a realistic path from the illuminator 301 to the camera 302.

If the optimization problem in equations 1 and 2 (or equations 3 and 4) is to be solved with the strict condition in equation 2 (or in equation 4), then the distance 620 should be zero. If, on the other hand, Lagrange relaxation is employed for the optimization, then small distances 620 may be allowed.

According to an embodiment, the step 1405 of estimating the first preliminary path in the method 1400 comprises:

obtaining a preliminary direction for light to leave the illuminator 301;

estimating a preliminary path 710 (see FIG. 7) for light leaving the illuminator 301 in the preliminary direction and getting reflected at the cornea 106;

forming a further distance 720 between the preliminary path and the camera 302;

determining, based on the further distance 720, an updated direction for light to leave the illuminator 301; and estimating the first preliminary path 410 (see FIG. 4) as a path for light leaving the illuminator 301 in the updated direction and getting reflected at the cornea 106.

In other words, the first preliminary path may be determined by trying different directions for light to leave the illuminator 301, and to use the distance 720 as a measure of how close the path is to a realistic path from the illuminator 301 to the camera 302. If the optimization problem in equations 1 and 2 (or equations 3 and 4) is to be solved with the strict condition in equation 2 (or in equation 4), then the distance 720 should be zero. If, on the other hand, Lagrange relaxation is employed for the optimization, then small distances 720 may be allowed.

As described above with reference to FIGS. 8 and 12, the second preliminary path estimated at step 1408 of the method 1400 may go from a point along the pupil edge 104 or the iris edge 102 to the camera 302. Hence, according to an embodiment, the step 1408 of estimating the second preliminary path comprises:

estimating, based on the preliminary position 109 of the eye 100 and the preliminary orientation 112 of the eye 100, a point in space along the edge; and estimating the second preliminary path as a path for light travelling from the point in space to the camera 302.

The point along the edge is exemplified in FIG. 8 by the point 811 along the pupil edge 104, and in FIG. 12 by the point 1211 along the iris edge 102. In the present embodiment, the step 1409 of estimating a point where the second preliminary path would appear to originate comprises:

estimating where the point (such as the point 811 or the point 1211) would appear in images captured by the camera by which image 900 (see FIG. 9) showing at least a portion of the edge was captured.

The position where the point 811 or the point 1211 would appear may for example be estimated by a projection in the camera 302.

As described above in relation to equations 3 and 4, the pupil 103 may change size as time passes, so the true pupil radius 118 may be unknown. Hence, if a point in space along the pupil edge 104 is to be estimated (for example the point 811 in FIG. 8), such an estimation may for example be based on a preliminary value for the pupil radius 118. In such a scenario, the method 1400 described above with reference to FIG. 14 may comprise determining an updated value for the pupil radius 118 using the objective function (for example the objective function in equation 3). If, for example, the objective function is a cost function which is to be minimized, the method 1400 may look for a value for the pupil radius 118 for which the objective function assumes a low value. The preliminary value for the pupil radius 118 may for example be an initial guess or start point of an optimization procedure.

According to an embodiment, the step 1408 of estimating the second preliminary path in the method 1400 comprises:

obtaining a preliminary direction for light to reach the camera 302; and estimating a preliminary path for light reaching the camera 302 in the preliminary direction after passing through at least a portion of the cornea 106 or after travelling from the sclera 117.

In the present embodiment, the method 1400 comprises determining, using the objective function, an updated position of the eye 100 in space and/or an updated orientation of the eye in space and/or an updated direction for light to reach the camera 302. This determination is performed subjected to a condition that the position 109 of the eye 100, the orientation 112 of the eye 100, and the direction for light to reach the camera 302 correspond to a path (such as the light path 810 in FIG. 8 or the light path 1200 in FIG. 12) for light travelling from the edge to the camera 302. In other words, although the second preliminary path (such as the light path 1010 in FIG. 10 or the light path 1310 in FIG. 13) may not originate at the edge of the iris 101 or the pupil 103, an updated position of the eye 100 in space and/or an updated orientation of the eye 100 in space and/or an updated direction for light to reach the camera 302 is determined such that a light path associated with these updated parameters does originate at the edge (like the light path 810 in FIG. 8 originating at the pupil edge 104 or the light path 1210 in FIG. 12 originating at the iris edge 102). This determination may for example be part of the step 1412 of determining an updated position and/or orientation of the eye 100 in space in the method 1400. It will be appreciated that in at least some cases, it may be sufficient to update only one of the position 109 of the eye 100 in space, the orientation 112 of the eye 100 in space, and the direction for light to reach the camera 302, to find a light path that goes from the edge to the camera 302 (like the light path 810 in FIG. 8). In other words, there may be no need to update all three of these to find such a light path.

According to an embodiment, the step 1408 of estimating the second preliminary path in the method 1400 comprises:

obtaining a preliminary direction for light to reach the camera 302;

estimating a preliminary path for light reaching the camera 302 in the preliminary direction after passing through at least a portion of the cornea 106 (like the path 1010 in FIG. 10) or after travelling from a sclera 117 of the eye 100 towards the camera 302 (like the path 1310 in FIG. 13);

forming a further distance (such as the distances 1020 and 1320 in FIGS. 10 and 13) between the preliminary path and the edge;

determining, based on the further distance, an updated direction for light to reach the camera 302; and estimating the second preliminary path as a path for light reaching the camera 302 in the updated direction after passing through at least a portion of the cornea 106 (like the path 810 in FIG. 8) or after travelling from a sclera 117 of the eye 100 towards the camera 302 (like the path 1310 in FIG. 13).

In other words, the second preliminary path may be determined by trying different directions for light to reach the camera 302, and to use the distance 1020 or 1320 as a measure of how close the path is to a realistic path from the pupil edge 104 or iris edge 102 to the camera 302. If the optimization problem in equations 1 and 2 (or equations 3 and 4) is to be solved with the strict condition in equation 2 (or in equation 4), then the distance 1020 or 1320 should be zero. If, on the other hand, Lagrange relaxation is employed for the optimization, then small distances 1020 or 1320 may be allowed.

According to an embodiment, the step 1408 of estimating the second preliminary path in the method 1400 comprises:
  obtaining a preliminary direction for light to leave a point along the edge (such as the point 1111 in FIG. 11);
  estimating a preliminary path (such as the path 1110 in FIG. 11) for light leaving the point along the edge in the preliminary direction;
  forming a further distance (such as the distance 1120 in FIG. 11) between the preliminary path and the camera 302;
  determining, based on the further distance, an updated direction for light to leave the point along the edge; and
  estimating the second preliminary path as a path (such as the path 810) for light leaving the edge in the updated direction.

In other words, the second preliminary path may be determined by trying different directions for light to leave the pupil edge 104 or the iris edge 102, and to use the distance 1120 (or a corresponding distance if the iris edge 102 is employed) as a measure of how close the path is to a realistic path from the edge to the camera 302.

If the optimization problem in equations 1 and 2 (or equations 3 and 4) is to be solved with the strict condition in equation 2 (or in equation 4), then the distance 1120 should be zero. If, on the other hand, Lagrange relaxation is employed for the optimization, then small distances 1120 may be allowed.

Figure 19:
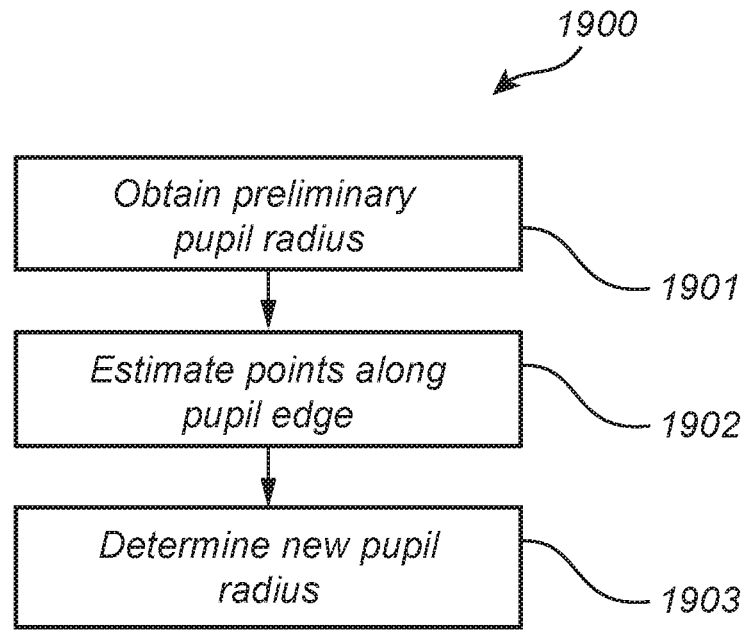
FIG. 19 is a flow chart of a scheme for dealing with an unknown pupil radius, which may be employed as part of the method in FIG. 14, according to an embodiment.

As described above with reference to FIG. 8, the edge referred to in the method 1400 may be the edge 104 of the pupil 103 of the eye 100. Since the pupil size varies over time, this may be regarded as an unknown, as described above in relation to equations 3 and 4. FIG. 19 is a flow chart of a scheme 1900 for how to handle the fact the true pupil radius 118 is unknown. This scheme 1900 may be employed in the method 1400 described above with reference to FIG. 14. Hence, according to an embodiment, the method 1400 comprises:
  obtaining 1901 a preliminary value for a radius 118 of the pupil 103;
  estimating 1902 points in space along the edge 104 of the pupil 103 based on the preliminary position 109 of the eye 100, the preliminary orientation 112 of the eye 100 and the preliminary value for the radius 118 of the pupil 103; and
  determining 1903, using the objective function, an updated value for the radius 118 of the pupil 103.

The method 1400 may for example look for a value of the pupil radius 118 for which the objective function may be minimized or maximized (depending on how the objective function has been defined). The method 1400 may for example strive to solve the optimization problem in equations 3 and 4.

As describe above with reference to FIG. 8, light from the pupil edge 104 passes through the cornea 106 on its way to the camera 302, so the light may be refracted at the cornea 106. Hence, according to an embodiment, the step 1408 of estimating the second preliminary path in the method 1400 may comprise estimating refraction of light at a surface of the cornea 106.

Figure 20:
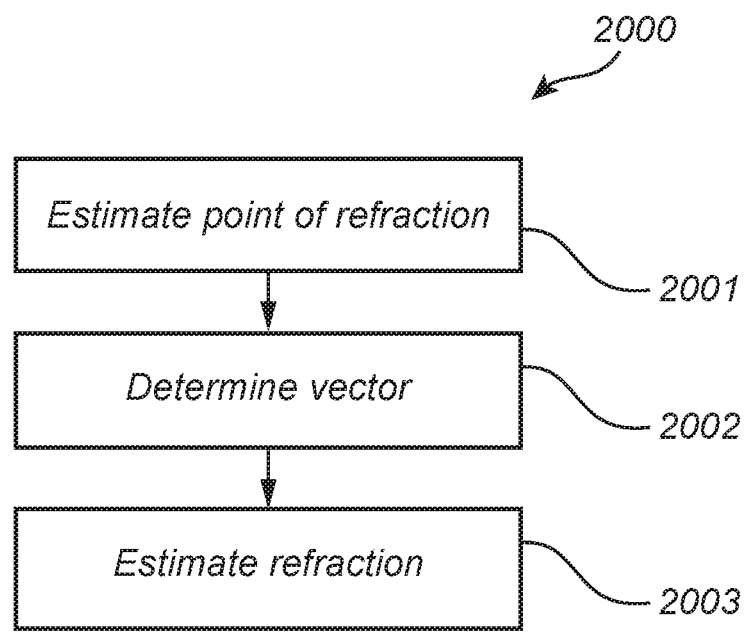
FIG. 20 is a flow chart of a scheme for estimating refraction at the cornea, which may be employed as part of the method in FIG. 14, according to an embodiment.

As described above with reference to FIG. 18, the cornea 106 is typically not perfectly spherical. FIG. 20 is a flow chart of a scheme 2000 for estimating refraction at the cornea 106. According to an embodiment, this scheme 2000 may be employed as part of the step 1408 of estimating the second preliminary path in the method 1400. According to the scheme 2000, estimating refraction of light at a surface of the cornea 106 comprises:
  estimating 2001 a point 812 (see FIG. 8) of refraction at the cornea 106;
  determining 2002 a vector 840 using a mapping (of function), wherein the mapping is adapted to map points at the cornea 106 to respective vectors; and
  estimating 2003 a refraction at the point 812 of refraction using the determined vector 840 as normal vector.

In other words, a mapping or function is employed to determine the vector which is to be employed as a normal vector when estimating how the refraction at the cornea 106 will be. The refraction may for example be computed via Snell's law. The mapping may for example be a normal mapping. Normal mappings are described further below in a separate section.

According to an embodiment, the step 2001 of estimating a point 812 of refraction comprises determining an intersection between a line and a surface (for example a spherical surface). In the present embodiment, the vector determined 2002 using the mapping forms an angle relative to a normal vector of the surface at the point of intersection. In other words, although a surface is employed to estimate 2001 the point 812 of refraction, the normal vector of that surface at the point 812 of refraction is not employed for estimating the refraction. Instead, the mapping (for example a normal mapping) is employed to determine 2002 a different vector to be employed as normal vector when estimating the reflection. It will be appreciated that the angle formed between the vector determined 2002 using the mapping and the normal vector of the surface is non-zero.

If a too complicated shape is employed in a cornea model, it may be difficult to determine the point 812 of refraction (which may be approximated as the point of intersection between the light ray and the cornea model). The cornea model may instead employ a relatively simple shape (such as a spherical surface), accompanied by a normal mapping which assigns normal vectors differing from the normal vectors of the surface. Thereby, the point 812 or refraction may be easily determined, and an appropriate normal vector may be assigned to take into account the fact that refraction at the cornea 106 may be more complicated than refraction at a simple surface such as a sphere. As mentioned above, the surface employed in the cornea model may for example be a spherical surface.

The methods described above with reference to FIGS. 4-20 represent a first aspect of the present disclosure. The gaze tracking system 300 described above with reference to FIG. 3 represents a second aspect of the present disclosure. The system 300 (or the processing circuitry 304 of the system 300) may for example be configured to perform the method of any of the embodiments of the first aspect described above. The system 300 (or the processing circuitry 304 of the system 300) may for example be configured to perform the method 1400 described above with reference to FIG. 14, optionally including any of the schemes described above with reference to FIGS. 17-20. As described above with reference to FIG. 3, the system 300 need not necessarily comprise all the elements shown in FIG. 3.

A third aspect of the present disclosure is represented by embodiments of a non-transitory computer-readable storage medium 307 storing instructions which, when executed by the gaze tracking system 300, cause the gaze tracking system 300 to perform the method of any of the embodiments of the first aspect described above (such as the method 1400 described above with reference to FIG. 14, optionally including the schemes described above with reference to FIGS. 17-20). As described above with reference to FIG. 3, the storage medium 307 need not necessarily be comprised in the gaze tracking system 300.

Normal Mapping

As described above with reference to FIGS. 18 and 20, the cornea model may comprise a spherical surface for computing intersections between light rays and the cornea, and a normal mapping method may be employed to model non-spherical and astigmatic properties of the cornea. This method defines the surface normal used when computing reflection of the cornea surface and refraction through the cornea surface. The normal mapping method may for example be employed at steps 1802 and 2002 in FIGS. 18 and 20.

Figure 21:
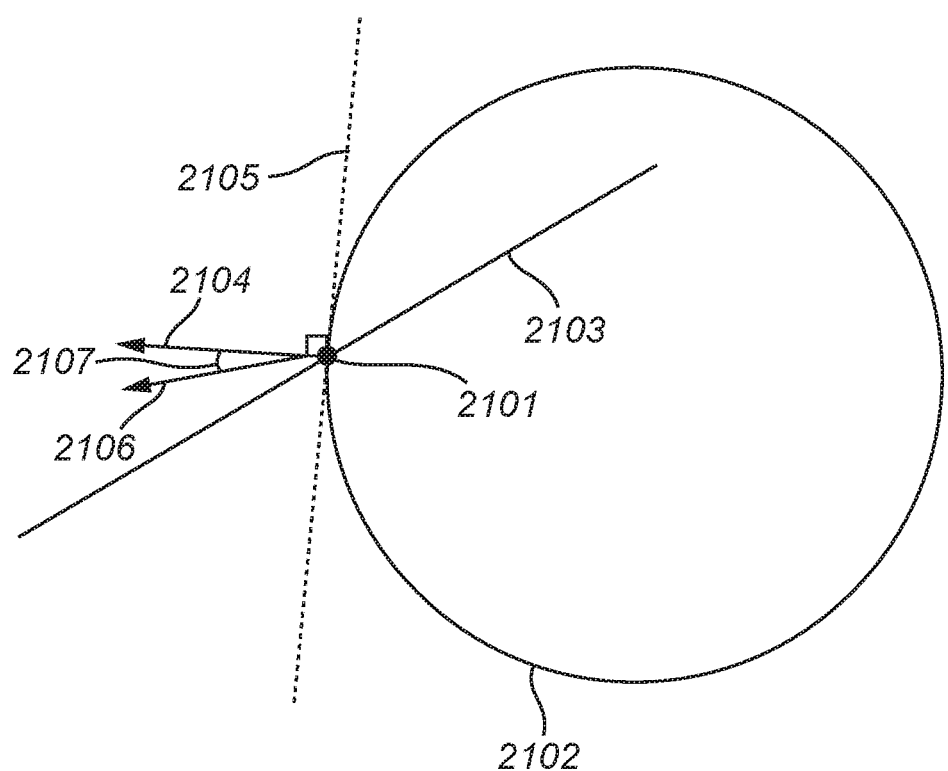
FIG. 21 illustrates use of a normal mapping, according to an embodiment.

FIG. 21 illustrates use of the normal mapping, according to an embodiment. First an intersection point 2101 is computed as an intersection between a spherical surface 2102 representing the cornea and a line 2103 representing the light ray. The surface 2102 has a normal vector 2104 which is normal to the tangent plane 2105 of the surface 2102 at the point 2101, but the normal mapping may provide a vector 2106 which forms a non-zero angle 2107 relative to the normal vector 2104. The vector 2106 provided by the normal mapping is employed for estimating refraction or reflection.

Given the intersection point 2101, a local coordinate system may be defined. The first component of this coordinate system is the normal of the sphere, which may for example be given by the difference between the cornea center position 107 and the intersection point. The second component of the coordinate system is the bi-tangent. It is formed by taking the cross product of the optical axis 112 and the normal. The last component in the coordinate system is the tangent, which is formed by taking the cross product of the normal and the bi-tangent. The effective surface normal 2106, which is used for reflection and/or refraction, is defined in this coordinate system. A normal map provides the coefficients for the effective surface normal for each component of the local coordinate system.

In an embodiment, the normal map is different for different radial angles on the cornea, to model astigmatism.

In an embodiment, the normal map is constant for different radial angles on the cornea and only stores the tangential component.

In an embodiment, the normal map is a bitmap.

In an embodiment, the normal map is a uni- or multivariate polynomial.

In an embodiment, reflection at the cornea surface is modeled using the vector formulation of reflection, with the effective surface normal provided by the normal map.

Pupil Model

As described above with reference to FIG. 19, points along the pupil edge 104 may need to be estimated. A pupil model may then be employed.

In an embodiment, the pupil 103 is modeled as circle on a plane with a surface normal aligned with the optical axis 112, at an (possibly variable) offset from the cornea center 107. The circle is either centered on the optical axis 112, or at an (possible variable) offset from the optical axis 112.

As described above with reference to FIG. 8, paths from points 811 along the pupil edge 104 may be traced to the camera 302. In one embodiment, four points on the pupil edge 104 are ray traced to the camera 302. Two of those points lie in the plane formed by the camera 302, the cornea center 107, and any point along the optical axis 112 (three points). The other two points lie in a plane orthogonal to the first plane, and which goes through the cornea center 107. The four ray traced points would give rise to four predicted points in the image 900. An ellipse may be fitted to those four predicted points, to be compared to the ellipse 901 provided by the image feature detector.

In an embodiment, the pupil ellipse is approximated as a circle.

MISCELLANEOUS

The person skilled in the art realizes that the present invention is by no means limited to the preferred embodiments described above. On the contrary, many modifications and variations are possible within the scope of the appended claims. For example, the embodiments described above with reference to FIGS. 1-20 may be combined to form further embodiments. Further, it will be appreciated that the gaze tracking system 300 shown in FIG. 3 is merely intended as an example, and that other gaze tracking systems may also perform the methods described above with reference to FIGS. 4-20. It will also be appreciated that the method steps described with reference to FIGS. 14 and 17-20 need not necessarily be performed in the specific order shown in these figures.

It will be appreciated that the refractions schematically illustrated in FIGS. 4, 6, 7, 10-13 are only shown for illustrative purposes, and that the angles of these example refractions may not necessarily be the same angles as one would get in real refractions. It will also be appreciated that the positions of predicted features indicated in FIGS. 5 and 9 are only examples, and do not necessarily match the positions which would actually be predicted for the light paths shown in FIGS. 4 and 8.

It will be appreciated that processing circuitry 304 (or a processor) may comprise a combination of one or more of a microprocessor, controller, microcontroller, central processing unit, digital signal processor, application-specific integrated circuit, field programmable gate array, or any other suitable computing device, resource, or combination of hardware, software and/or encoded logic operable to provide computer functionality, either alone or in conjunction with other computer components (such as a memory or storage medium).

It will also be appreciated that a memory or storage medium 307 (or a computer-readable medium) may comprise any form of volatile or non-volatile computer readable memory including, without limitation, persistent storage, solid-state memory, remotely mounted memory, magnetic media, optical media, random access memory (RAM), read-only memory (ROM), mass storage media (for example, a hard disk), removable storage media (for example, a flash drive, a Compact Disk (CD) or a Digital Video Disk (DVD)), and/or any other volatile or non-volatile, non-transitory device readable and/or computer-executable memory devices that store information, data, and/or instructions that may be used by a processor or processing circuitry.

Additionally, variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. In the claims, the word "or" is not to be interpreted as an exclusive or (sometimes referred to as "XOR"). On the contrary, expressions such as "A or B" covers all the cases "A and not B", "B and not A" and "A and B", unless otherwise indicated. The mere fact that certain measures are recited in mutually different dependent claims does not indicate that a combination of these measures cannot be used to advantage. Any reference signs in the claims should not be construed as limiting the scope.

The invention claimed is:

1. A gaze tracking method comprising:
    obtaining one or more images of an eye, wherein an image of said one or more images has been captured by a camera at a time instance while the eye was illuminated by an illuminator, wherein the image captured by the camera shows a first reflection of the illuminator at a cornea of the eye, wherein an image of said one or more images has been captured by a camera at said time instance and shows at least a portion of an edge, wherein the edge is:
        an edge of a pupil of the eye; or
        an edge of an iris of the eye;
    detecting a position of the first reflection in the image showing the first reflection;
    detecting at least a portion of the edge in the image showing at least a portion of the edge;
    obtaining a preliminary position of the eye in space and a preliminary orientation of the eye in space;
    estimating, based on the preliminary position of the eye and the preliminary orientation of the eye, a first preliminary path for light travelling, via a reflection at the cornea, towards the camera by which said image showing the first reflection was captured;
    estimating a position where the reflection from the first preliminary path would appear in images of the eye captured by the camera by which said image showing the first reflection was captured;
    forming a first distance between the detected position of the first reflection in said image showing the first reflection and the estimated position where the reflection from the first preliminary path would appear;
    estimating, based on the preliminary position of the eye and the preliminary orientation of the eye, a second preliminary path for light travelling through at least a portion of the cornea of the eye towards the camera by which said image showing at least a portion of the edge was captured or for light travelling from a sclera of the eye towards the camera by which said image showing at least a portion of the edge was captured;
    estimating a position where the second preliminary path would appear to originate in images of the eye captured by the camera by which said image showing at least a portion of the edge was captured;
    forming a second distance between the edge and the estimated position where the second preliminary path would appear to originate;
    forming an objective function based on at least the first and second distances; and
    determining, using the objective function, an updated position of the eye in space and/or an updated orientation of the eye in space.

2. The method of claim 1, wherein said image showing the first reflection coincides with said image showing at least a portion of the edge.

3. The method of claim 1, wherein a person is equipped with glasses, wherein said eye is an eye of the person,
    and wherein estimating the first preliminary path comprises:
        estimating refraction of light at one or more surfaces of the glasses;
    and/or wherein estimating the second preliminary path comprises:
        estimating refraction of light at one or more surfaces of the glasses.

4. The method of claim 3, further comprising:
    obtaining a position and/or orientation of the glasses,
    wherein the refraction of light at one or more surfaces of the glasses is estimated based in the obtained position and/or orientation of the glasses.

5. The method of claim 4, further comprising:
    monitoring a head pose of the user,
    wherein the position and/or orientation of the glasses is obtained based on the head pose.

6. The method of claim 1, wherein estimating the first preliminary path comprises:
    estimating a point of reflection at the cornea;
    determining a vector using a mapping, wherein the mapping is adapted to map points at the cornea to respective vectors; and
    estimating a reflection at the point of reflection using the determined vector as a normal vector.

7. The method of claim 6, wherein estimating a point of reflection at the cornea comprises:
    determining an intersection between a line and a surface,
    and wherein the determined vector forms an angle relative to a normal vector of said surface at the point of intersection.

8. The method of claim 1, wherein the first preliminary path is a preliminary path for light travelling from the illuminator, via a reflection at the cornea, to the camera by which said image showing the first reflection was captured.

9. The method of claim 1, wherein estimating the first preliminary path comprises:
    obtaining a preliminary direction for light to reach the camera; and
    estimating the first preliminary path as a preliminary path for light reaching the camera in the preliminary direction via a reflection at the cornea,
    wherein the method comprises:
    determining, using the objective function, an updated position of the eye in space and/or an updated orientation of the eye in space and/or an updated direction for light to reach the camera, wherein the determining is performed subjected to a condition that the position of the eye, the orientation of the eye, and the direction for light to reach the camera correspond to a path for light travelling from the illuminator to the camera via a reflection at the cornea.

10. The method of claim 1, wherein estimating, the first preliminary path comprises:
    obtaining a preliminary direction for light to reach the camera;

estimating a preliminary path for light reaching the camera in the preliminary direction via a reflection at the cornea;
forming a further distance between the preliminary path and the illuminator;
determining, based on the further distance, an updated direction for light to reach the camera; and
estimating the first preliminary path as a path for light reaching the camera in the updated direction via a reflection at the cornea,
or wherein estimating the first preliminary path comprises:
obtaining a preliminary direction for light to leave the illuminator;
estimating a preliminary path for light leaving the illuminator in the preliminary direction and getting reflected at the cornea;
forming a further distance between the preliminary path and the camera;
determining, based on the further distance, an updated direction for light to leave the illuminator; and
estimating the first preliminary path as a path for light leaving the illuminator in the updated direction and getting reflected at the cornea.

11. The method of claim 1, wherein estimating the second preliminary path comprises:
estimating, based on the preliminary position of the eye and the preliminary orientation of the eye, a point in space along said edge; and
estimating the second preliminary path as a path for light travelling from the point in space to the camera by which said image showing at least a portion of the edge was captured;
and wherein estimating a point where the second preliminary path would appear to originate in images of the eye captured by the camera by which said image showing at least a portion of the edge was captured comprises:
estimating where said point would appear in images captured by the camera by which said image showing at least a portion of the edge was captured.

12. The method of claim 11, wherein said edge is an edge of the pupil of the eye, wherein the method further comprises:
obtaining a preliminary value for a radius of the pupil,
wherein said point in space along said edge is estimated based on the preliminary position of the eye, the preliminary orientation of the eye and the preliminary value for the radius of the pupil, and wherein the method further comprises:
determining, using the objective function, an updated value for the radius of the pupil.

13. The method of claim 1, wherein estimating the second preliminary path comprises:
obtaining a preliminary direction for light to reach the camera; and
estimating a preliminary path for light reaching the camera in the preliminary direction after passing through at least a portion of the cornea or after travelling from the sclera,
wherein the method comprises:
determining, using the objective function, an updated position of the eye in space and/or an updated orientation of the eye in space and/or an updated direction for light to reach the camera, wherein the determining is performed subjected to a condition that the position of the eye, the orientation of the eye, and the direction for light to reach the camera correspond to a path for light travelling from the edge to the camera.

14. The method of claim 1, wherein estimating the second preliminary path comprises:
obtaining a preliminary direction for light to reach the camera;
estimating a preliminary path for light reaching the camera in the preliminary direction after passing through at least a portion of the cornea or after travelling from a sclera of the eye towards the camera,
forming a further distance between the preliminary path and the edge;
determining, based on the further distance, an updated direction for light to reach the camera; and
estimating the second preliminary path as a path for light reaching the camera in the updated direction after passing through at least a portion of the cornea or after travelling from a sclera of the eye towards the camera,
or wherein estimating the second preliminary path comprises:
obtaining a preliminary direction for light to leave a point along the edge;
estimating a preliminary path for light leaving the point along the edge in the preliminary direction;
forming a further distance between the preliminary path and the camera;
determining, based on the further distance, an updated direction for light to leave the point along the edge; and
estimating the second preliminary path as a path for light leaving the edge in the updated direction.

15. The method of claim 13, wherein said edge is the edge of the pupil of the eye, and wherein the method comprises:
obtaining a preliminary value for a radius of the pupil;
estimating points in space along said edge based on the preliminary position of the eye, the preliminary orientation of the eye and the preliminary value for the radius of the pupil; and
determining, using the objective function, an updated value for the radius of the pupil.

16. The method of claim 1, wherein estimating the second preliminary path comprises:
estimating refraction of light at a surface of the cornea.

17. The method of claim 16, wherein estimating refraction of light at a surface of the cornea comprises:
estimating a point of refraction at the cornea;
determining a vector using a mapping, wherein the mapping is adapted to map points at the cornea to respective vectors; and
estimating a refraction at the point of refraction using the determined vector as normal vector.

18. The method of claim 1, wherein:
the updated position of the eye in space and/or the updated orientation of the eye in space is determined for reducing a value of the objective function; or
the updated position of the eye in space and/or the updated orientation of the eye in space is determined for increasing a value of the objective function.

19. A gaze tracking system comprising processing circuitry configured to:
obtain one or more images of an eye, wherein an image of said one or more images has been captured by a camera at a time instance while the eye was illuminated by an illuminator, wherein the image captured by the camera shows a first reflection of the illuminator at a cornea of the eye, wherein an image of said one or more images has been captured by a camera at said time instance and shows at least a portion of an edge, wherein the edge is:
an edge of a pupil of the eye; or
an edge of an iris of the eye;
detect a position of the first reflection in the image showing the first reflection;
detect at least a portion of the edge in the image showing at least a portion of the edge;
obtain a preliminary position of the eye in space and a preliminary orientation of the eye in space;
estimate, based on the preliminary position of the eye and the preliminary orientation of the eye, a first preliminary path for light travelling, via a reflection at the cornea, towards the camera by which said image showing the first reflection was captured;
estimate a position where the reflection from the first preliminary path would appear in images of the eye captured by the camera by which said image showing the first reflection was captured;
form a first distance between the detected position of the first reflection in the image showing the first reflection and the estimated position where the reflection from the first preliminary path would appear;
estimate, based on the preliminary position of the eye and the preliminary orientation of the eye, a second preliminary path for light travelling through at least a portion of the cornea of the eye towards the camera by which said image showing at least a portion of the edge was captured or for light travelling from a sclera of the eye towards the camera by which said image showing at least a portion of the edge was captured;
estimate a position where the second preliminary path would appear to originate in images of the eye captured by the camera by which said image showing at least a portion of the edge was captured;
form a second distance between the edge and the estimated position where the second preliminary path would appear to originate;
form an objective function based on at least the first and second distances; and
determine, using the objective function, an updated position of the eye in space and/or an updated orientation of the eye in space.

20. A non-transitory computer-readable storage medium storing instructions which, when executed by a gaze tracking system, cause the gaze tracking system to:
obtain one or more images of an eye, wherein an image of said one or more images has been captured by a camera at a time instance while the eye was illuminated by an illuminator, wherein the image captured by the camera shows a first reflection of the illuminator at a cornea of the eye, wherein an image of said one or more images has been captured by a camera at said time instance and shows at least a portion of an edge, wherein the edge is:
an edge of a pupil of the eye; or
an edge of an iris of the eye;
detect a position of the first reflection in the image showing the first reflection;
detect at least a portion of the edge in the image showing at least a portion of the edge;
obtain a preliminary position of the eye in space and a preliminary orientation of the eye in space;
estimate, based on the preliminary position of the eye and the preliminary orientation of the eye, a first preliminary path for light travelling, via a reflection at the cornea, towards the camera by which said image showing the first reflection was captured;
estimate a position where the reflection from the first preliminary path would appear in images of the eye captured by the camera by which said image showing the first reflection was captured;
form a first distance between the detected position of the first reflection in the image showing the first reflection and the estimated position where the reflection from the first preliminary path would appear;
estimate, based on the preliminary position of the eye and the preliminary orientation of the eye, a second preliminary path for light travelling through at least a portion of the cornea of the eye towards the camera by which said image showing at least a portion of the edge was captured or for light travelling from a sclera of the eye towards the camera by which said image showing at least a portion of the edge was captured;
estimate a position where the second preliminary path would appear to originate in images of the eye captured by the camera by which said image showing at least a portion of the edge was captured;
form a second distance between the edge and the estimated position where the second preliminary path would appear to originate;
form an objective function based on at least the first and second distances; and
determine, using the objective function, an updated position of the eye in space and/or an updated orientation of the eye in space.

* * * * *